United States Patent
Jimenez et al.

(10) Patent No.: US 12,076,257 B2
(45) Date of Patent: Sep. 3, 2024

(54) DELIVERY SYSTEMS FOR STENTS HAVING PROTRUDING FEATURES

(71) Applicant: ReFlow Medical, Inc., San Clemente, CA (US)

(72) Inventors: Teodoro S. Jimenez, Aliso Viejo, CA (US); John Fulkerson, Rancho Santa Margarita, CA (US); Isa Rizk, San Clemente, CA (US); Jihad Ali Mustapha, Ada, MI (US)

(73) Assignee: ReFlow Medical, Inc., San Clemente, CA (US)

( * ) Notice: Subject to any disclaimer, the term of this patent is extended or adjusted under 35 U.S.C. 154(b) by 0 days.

(21) Appl. No.: 15/947,691

(22) Filed: Apr. 6, 2018

(65) Prior Publication Data
US 2018/0289517 A1    Oct. 11, 2018

Related U.S. Application Data

(60) Provisional application No. 62/482,600, filed on Apr. 6, 2017.

(51) Int. Cl.
*A61F 2/92* (2013.01)
*A61F 2/848* (2013.01)
(Continued)

(52) U.S. Cl.
CPC ............. *A61F 2/92* (2013.01); *A61F 2/848* (2013.01); *A61F 2/90* (2013.01); *A61F 2/966* (2013.01);
(Continued)

(58) Field of Classification Search
CPC .. A61F 2/92; A61F 2/848; A61F 2/958; A61F 2/90; A61F 2250/0067;
(Continued)

(56) References Cited

U.S. PATENT DOCUMENTS

| | | | |
|---|---|---|---|
| 5,445,646 A | * | 8/1995 | Euteneuer ............... A61F 2/966 606/198 |
| 5,639,274 A | * | 6/1997 | Fischell .................. A61F 2/958 604/104 |

(Continued)

FOREIGN PATENT DOCUMENTS

| | | |
|---|---|---|
| CN | 101247777 A | 8/2008 |
| EP | 0701800 | 3/1996 |

(Continued)

OTHER PUBLICATIONS

International Search Report and Written Opinion from PCT/US2018/026581, dated Aug. 1, 2018, 12 pages.

(Continued)

*Primary Examiner* — Brooke Labranche
(74) *Attorney, Agent, or Firm* — BAKERHOSTETLER

(57) ABSTRACT

Delivery systems for expandable elements, such as stents or scaffolds having spikes, flails, or other protruding features for delivering drugs and/or penetrating target tissue within a human patient and associated methods for using such systems. The delivery systems can be configured to deliver and position expandable structures within a body lumen (e.g., vessel). In addition, these delivery systems can also be configured to deploy and expand the expandable structures in the body lumen. The delivery systems can further be configured to engage with the expanded structure and collapse the structure for removal from the body lumen. The delivery systems can be configured to deliver another expandable structure or the same expandable structure to another body lumen, or the same body lumen, in a single procedure or during a plurality of procedures.

18 Claims, 17 Drawing Sheets

(51) Int. Cl.
*A61F 2/90* (2013.01)
*A61F 2/966* (2013.01)
*A61L 31/16* (2006.01)
*A61F 2/95* (2013.01)
*A61F 2/958* (2013.01)

(52) U.S. Cl.
CPC ....... *A61L 31/16* (2013.01); *A61F 2002/8483* (2013.01); *A61F 2002/9528* (2013.01); *A61F 2002/9534* (2013.01); *A61F 2/958* (2013.01); *A61F 2220/0016* (2013.01); *A61F 2250/0067* (2013.01); *A61F 2250/0098* (2013.01); *A61L 2300/416* (2013.01)

(58) Field of Classification Search
CPC ...... A61F 2002/8483; A61F 2220/0016; A61F 2250/0098; A61L 31/16; A61L 2300/416; A61M 25/10; A61M 29/00
See application file for complete search history.

(56) References Cited

U.S. PATENT DOCUMENTS

| | | | |
|---|---|---|---|
| 5,843,167 A | 12/1998 | Dwyer et al. | |
| 6,113,579 A * | 9/2000 | Eidenschink | A61M 25/0068 604/264 |
| 6,221,096 B1 * | 4/2001 | Aiba | A61F 2/86 606/108 |
| 6,425,915 B1 | 7/2002 | Khosravi et al. | |
| 6,613,075 B1 | 9/2003 | Healy et al. | |
| 6,991,617 B2 | 1/2006 | Hektner et al. | |
| 7,520,903 B2 | 4/2009 | Ferreyrol | |
| 7,753,945 B2 | 7/2010 | Bruun et al. | |
| 8,128,687 B2 | 3/2012 | Rao | |
| 8,128,676 B2 | 6/2012 | Cummings | |
| 8,337,542 B2 | 12/2012 | Jantzen et al. | |
| 8,414,635 B2 * | 4/2013 | Hyodoh | D04C 3/48 623/1.11 |
| 8,414,909 B2 | 4/2013 | Wang | |
| 8,623,066 B2 | 1/2014 | Looi et al. | |
| 8,690,822 B2 | 4/2014 | Papp | |
| 8,758,420 B2 | 6/2014 | Dorn et al. | |
| 8,764,814 B2 | 7/2014 | Solem | |
| 8,771,340 B2 | 7/2014 | Densford | |
| 8,926,683 B2 | 1/2015 | Gill et al. | |
| 8,956,398 B2 | 2/2015 | George et al. | |
| 9,198,784 B2 | 12/2015 | Andreas et al. | |
| 9,220,618 B2 | 12/2015 | Igaki et al. | |
| 9,445,929 B2 | 9/2016 | Longo et al. | |
| 9,566,367 B2 | 2/2017 | Stekker et al. | |
| 9,597,206 B2 | 3/2017 | Seddon et al. | |
| 9,675,473 B2 | 6/2017 | Clerc et al. | |
| 9,724,220 B2 | 8/2017 | Rasmussen | |
| 9,770,575 B2 | 9/2017 | Wesselmann et al. | |
| 9,814,608 B2 | 11/2017 | Clerc et al. | |
| 9,855,160 B2 | 1/2018 | Armstrong et al. | |
| 10,004,615 B2 | 6/2018 | Sherry | |
| 10,039,659 B2 | 8/2018 | Bialas et al. | |
| 10,307,273 B2 | 6/2019 | Rubesch et al. | |
| 10,342,684 B2 | 7/2019 | Firstenberg et al. | |
| 10,668,188 B2 | 6/2020 | Wang | |
| 2003/0125751 A1 | 7/2003 | Griffin et al. | |
| 2003/0135751 A1 | 7/2003 | O'Donnell et al. | |
| 2004/0064093 A1 * | 4/2004 | Hektner | A61M 25/104 604/103.01 |
| 2005/0096731 A1 | 5/2005 | Looi et al. | |
| 2007/0043419 A1 | 2/2007 | Nikolchev et al. | |
| 2007/0055299 A1 * | 3/2007 | Ishimaru | A61F 2/07 606/191 |
| 2008/0109065 A1 | 5/2008 | Bowe | |
| 2008/0243230 A1 * | 10/2008 | Lootz | A61F 2/91 623/1.15 |
| 2010/0069838 A1 * | 3/2010 | Weber | A61M 31/002 604/103.02 |
| 2010/0202487 A1 | 8/2010 | Sartorius et al. | |
| 2010/0204770 A1 | 8/2010 | Mas et al. | |
| 2010/0256725 A1 * | 10/2010 | Rasmussen | A61F 2/07 623/1.11 |
| 2012/0016454 A1 * | 1/2012 | Jantzen | A61F 2/966 623/1.11 |
| 2012/0101560 A1 * | 4/2012 | Kluck | A61M 29/02 623/1.11 |
| 2012/0172844 A1 * | 7/2012 | Mullen | A61M 25/09 604/528 |
| 2016/0206344 A1 * | 7/2016 | Bruzzi | A61B 17/221 |
| 2016/0242940 A1 | 8/2016 | Krautkremer et al. | |
| 2017/0056154 A1 | 3/2017 | Greenberg et al. | |
| 2018/0303594 A1 | 10/2018 | Eller et al. | |
| 2018/0360589 A1 | 12/2018 | Nolan et al. | |
| 2019/0167456 A1 | 6/2019 | Collins et al. | |
| 2020/0139017 A1 | 5/2020 | Meyer-Kobbe et al. | |
| 2020/0171214 A1 | 6/2020 | Dietz | |
| 2020/0214825 A1 | 7/2020 | Gassler | |

FOREIGN PATENT DOCUMENTS

| | | |
|---|---|---|
| EP | 1506747 | 2/2005 |
| EP | 2414021 | 2/2012 |
| EP | 2531229 | 12/2012 |
| EP | 2545887 | 1/2013 |
| EP | 2550030 | 1/2013 |
| JP | H 08-299456 | 11/1996 |
| JP | 2001-511023 | 8/2001 |
| JP | 2008-543399 | 12/2008 |
| JP | 2010-504821 | 2/2010 |
| WO | WO 2018/213352 | 11/2018 |
| WO | WO 2020/101675 | 5/2020 |
| WO | WO 2020/172560 | 8/2020 |

OTHER PUBLICATIONS

Extended European Search Report from European Patent Application No. 18780456.2, dated Jan. 28, 2021, 19 pages.
Partial European Search Report from European Patent Application No. 18780456.2, dated Sep. 3, 2017 pages.
Chinese Office Action from 2018800336201, dated May 8, 2021, 21 pages including English language translation.
Japanese Office Action from Japanese Patent Application No. 2019-554854, dated Sep. 28, 2021, 15 pages including machine-generated English language translation.
Japanese Office Action from Japanese Patent Application No. 2019-554854, dated Jun. 9, 2022, 5 pages including English language translation.
Chinese Office Action from Chinese Patent Application No. 2018800336201, dated Jan. 20, 2022, 20 pages including English language translation.
Chinese Office Action from Chinese Patent Application No. 201880033620.1, dated Oct. 8, 2022, 23 pages including machine-generated English language translation.
Japanese Office Action from Japanese Patent Application No. 2022-162070, dated Jul. 12, 2023, 15 pages including English language translation.
Australian Office Action from Australian Patent Application No. 20182449936, dated May 4, 2023, 6 pages.
Chinese Office Action from Chinese Patent Application No. 201880033620.1, dated May 29, 2023 (no translation).
Australian Notice of Acceptance from Australian Patent Application No. 20182449936, dated Apr. 18, 2024, 3 pages.

\* cited by examiner

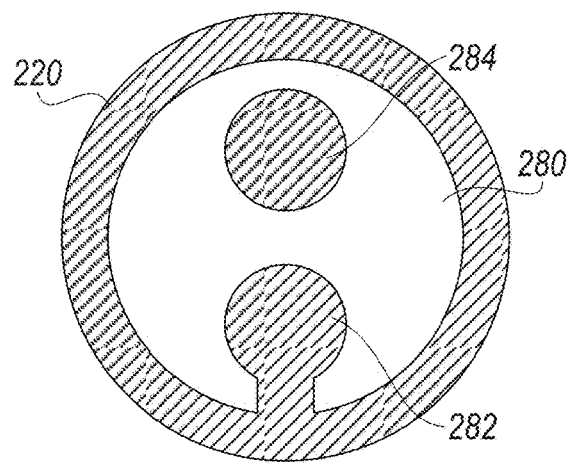
FIG. 2D
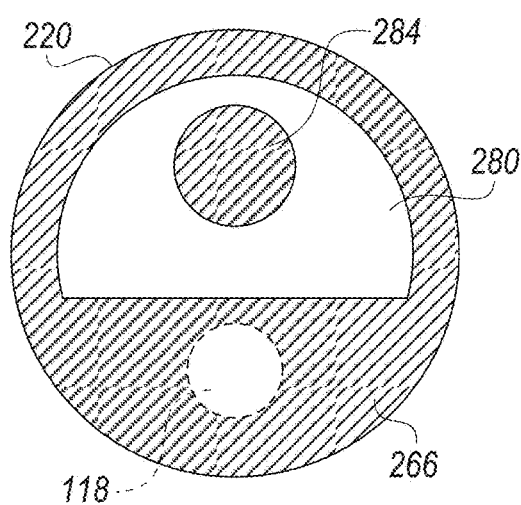 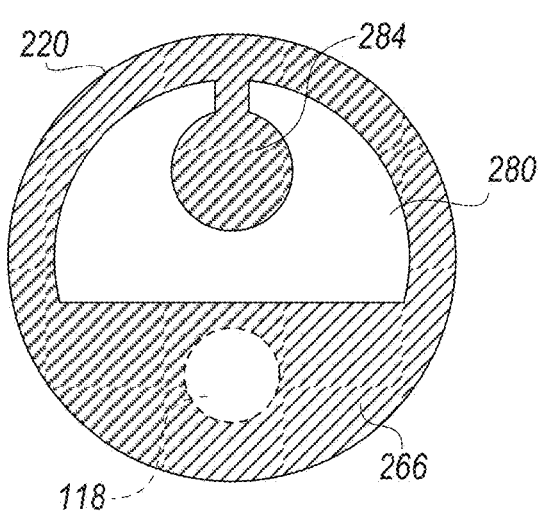
FIG. 2E        FIG. 2F

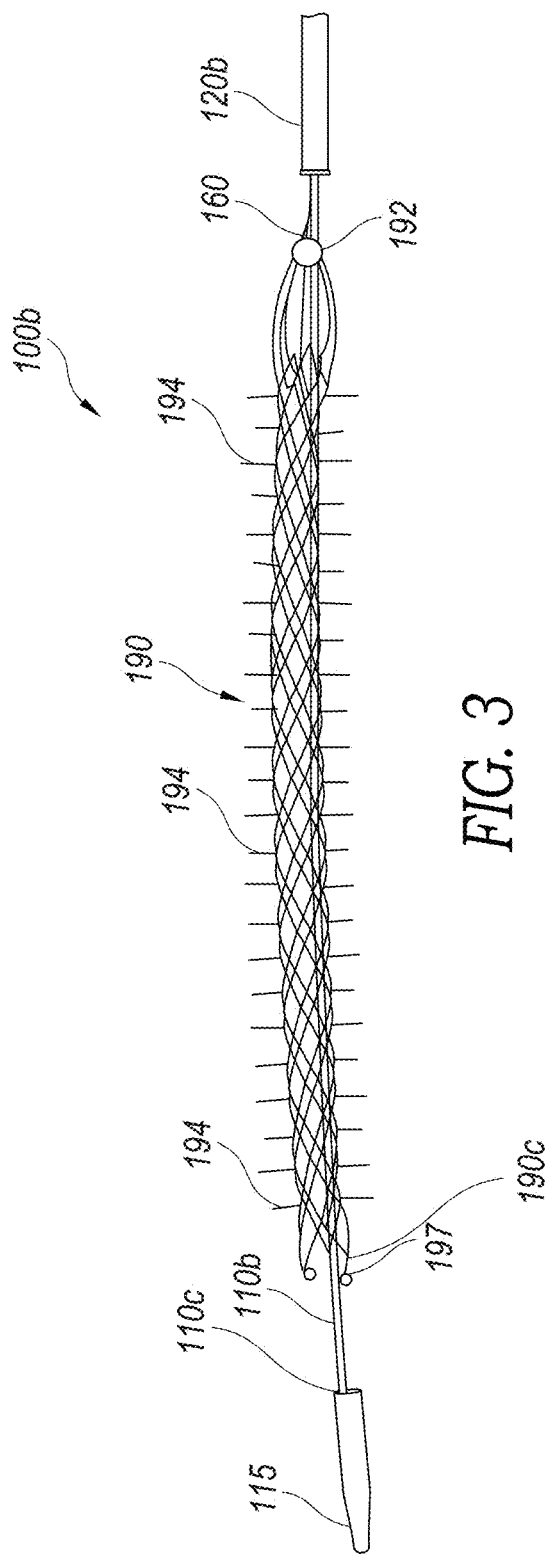

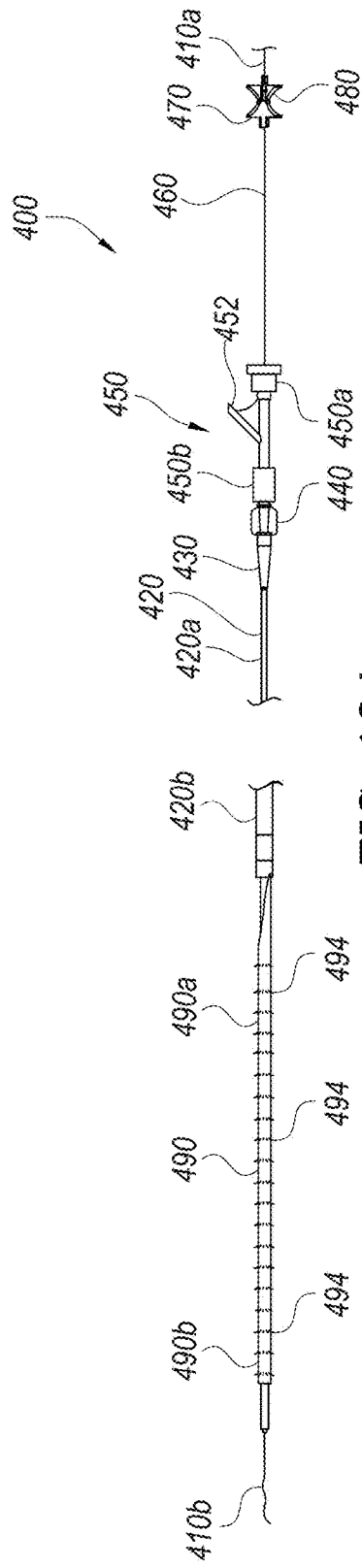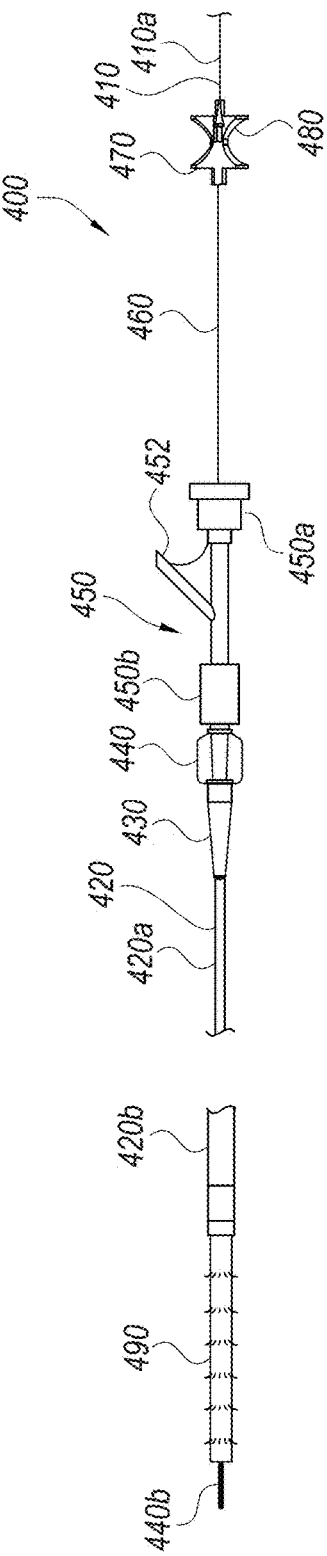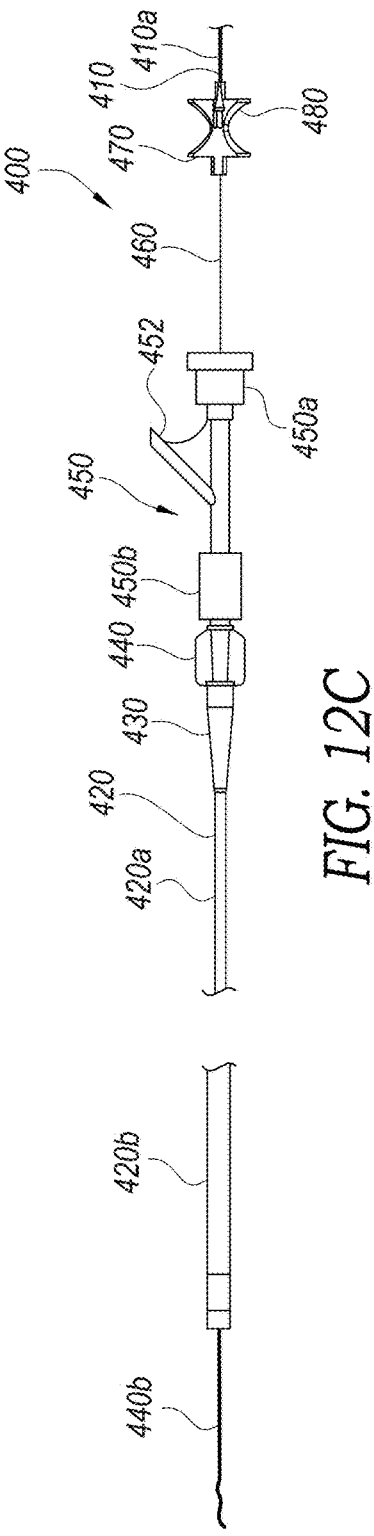
FIG. 12A
FIG. 12B
FIG. 12C

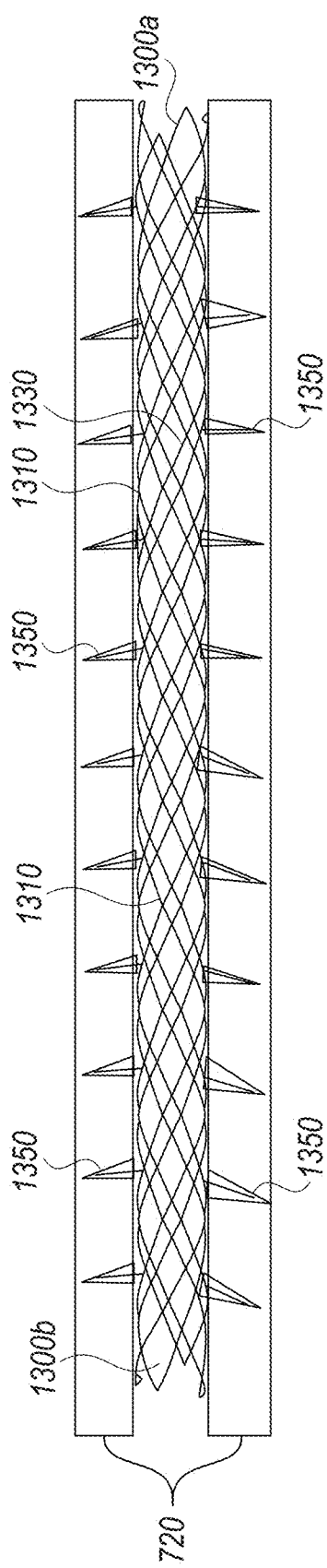

DELIVERY SYSTEMS FOR STENTS HAVING PROTRUDING FEATURES

CROSS-REFERENCE TO RELATED APPLICATIONS

This application claims the benefit of U.S. Provisional Application No. 62/482,600, entitled "DELIVERY SYSTEMS FOR STENTS HAVING PROTRUDING DRUG-DELIVERY FEATURES AND ASSOCIATED DEVICES AND METHODS," filed Apr. 6, 2017, the entirety of which is incorporated herein by reference.

TECHNICAL FIELD

The present description relates generally to delivery systems for expandable elements, such as stents or scaffolds having spikes, flails, or other protruding features for delivering drugs and/or penetrating target tissue within a human patient.

BACKGROUND

A variety of devices can be used to deliver drugs at desired treatment locations within a patient. For example, a drug-eluting stent (DES) can be positioned at the location of a stenosis (arterial narrowing) caused by arteriosclerosis. DESs generally include a drug containing polymer coated over a metal stent or scaffold, or a bioresorbable stent or scaffold composed of a drug-containing polymer. After a DES is delivered to a treatment location within a body lumen (e.g., vessel), it is expanded against a wall of the body lumen (e.g., a vessel wall) and the drug is released via direct contact with the wall. Direct delivery of the drug to the vessel wall enables significantly lower doses than those required via other delivery means (e.g., pills or injections). However, depending on the design of the underlying stent or scaffold, 85% or more of the stented vessel wall area may not be in contact with the stent struts. Accordingly, significant diseased portions of the vessel wall may not receive a desired dose or delivery of the drug will not be uniform throughout the treatment site. Additionally, portions of the DES may be in contact with blood, arterial plaque and/or with other fluid or materials within the vessel lumen that are not intended delivery sites for the drug. These issues can result in drug tissue concentrations that are lower than desired or less uniform than desired.

Drug-eluting balloons (DEBs), and non-drug-eluting balloons, provide an alternative to DESs, and can address some of the limitations discussed above. For example, DEBs can also be delivered to a desired treatment location and expanded against a vessel wall to release a drug. DEBs, however, can include a coating of the drug over an entire surface area of the balloon that expands to be in uniform contact with the vessel wall. Accordingly, DEBs can provide a more uniform dose to the adjacent vessel tissue. Additionally, when used in conjunction with angioplasty, the drug can be delivered at the location and time of any vessel damage that occurs during the procedure. Even so, DEBs also have several limitations. For example, during the delivery of the drug (i.e., when the balloon is inflated), blood flow in the associated vessel is stopped or severely obstructed, and no other treatment devices can be passed through the vessel. Additionally, both DEBs and existing DESs fail to provide drug-delivery at all locations along an adjacent vessel wall. Specifically, uneven vessel walls, obstructions, contours, or other features can prevent the balloon surface or stent struts from reaching portions of the vessel wall. Moreover, existing DESs and DEBs do not provide for drug-delivery into the vessel wall (i.e., penetration of the vessel wall for drug-delivery within the tissue itself).

BRIEF DESCRIPTION OF THE DRAWINGS

Many aspects of the present technology can be better understood with reference to the following drawings. The components in the drawings are not necessarily to scale. Instead, emphasis is placed on illustrating clearly the principles of the present technology. For ease of reference, throughout this disclosure identical reference numbers may be used to identify identical or at least generally similar or analogous components or features.

FIGS. 2A-2F are enlarged, cross-sectional views of various configurations of a region of the delivery system of FIG. 1 taken along line 2-2.

FIG. 3 is an enlarged, partially schematic side view of a distal portion of the delivery system of FIG. 1 configured in accordance with an embodiment of the present technology.

FIGS. 12A-12C are partially schematic side views of the delivery system of FIG. 4 in various stages of the partially retracted state and configured in accordance with an embodiment of the present technology.

FIG. 13 is a partially schematic side view of a drug-eluting expandable structure having drug-delivery features in the deployed state within a body lumen and configured in accordance with an embodiment of the present technology.

FIGS. 14A and 14B are isometric views of portions of drug-eluting expandable structures having drug-delivery features configured in accordance with embodiments of the present technology.

Figure 1:
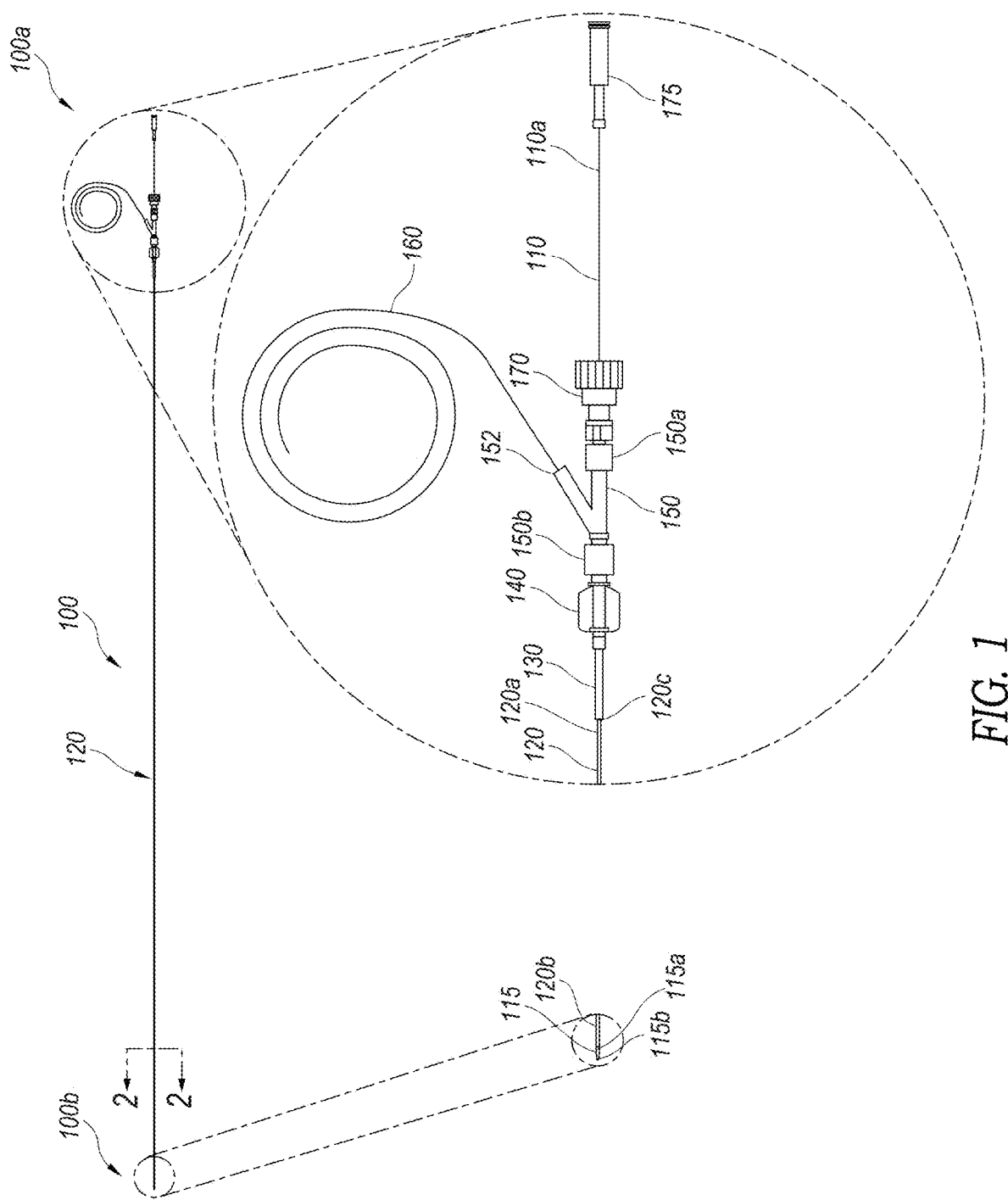
FIG. 1 is a partially schematic side view of a delivery system in a delivery state (e.g., low-profile or collapsed configuration) configured in accordance with an embodiment of the present technology.

In one or more implementations, not all of the depicted components in each figure may be required, and one or more implementations may include additional components not shown in a figure. Variations in the arrangement and type of the components may be made without departing from the scope of the subject disclosure. Additional components, different components, or fewer components may be utilized within the scope of the subject disclosure.

DETAILED DESCRIPTION

The detailed description set forth below is intended as a description of various implementations and is not intended to represent the only implementations in which the subject technology may be practiced. As those skilled in the art would realize, the described implementations may be modified in various different ways, all without departing from the scope of the present disclosure. Accordingly, the drawings and description are to be regarded as illustrative in nature and not restrictive.

The following disclosure describes various embodiments of delivery systems for expandable structures, such as stents or scaffolds, having spikes, flails, or other protruding features for delivering drugs and/or penetrating target tissue within a human patient, and associated devices and methods. The delivery systems can be configured to deliver and position expandable structures within a body lumen (e.g., vessel). In addition, these delivery systems can also be configured to deploy and expand the expandable structures in the body lumen. The delivery systems can further be configured to engage with the expanded structure and collapse the structure for removal from the body lumen. In some embodiments, the delivery systems can be configured to deliver another expandable structure or the same expandable structure to another body lumen, or the same body lumen, in a single procedure or during a plurality of procedures. Such delivery systems are expected to simplify and expedite transluminal procedures to more effectively deliver and position expandable structures within target tissues. Additionally, the delivery systems can be used with more than one procedure, such as deployment of an expandable structure, when configured to re-capture the deployed expandable structure. Still other embodiments of delivery systems configured in accordance with the present technology may include different features and/or procedures for using such systems.

Certain details are set forth in the following description and FIGS. 1-16 to provide a thorough understanding of various embodiments of the disclosure. To avoid unnecessarily obscuring the description of the various embodiments of the disclosure, other details describing well-known structures and systems often associated with expandable structures, drug-delivery features, and the components or devices associated with the manufacture of such structures are not set forth below. Moreover, many of the details and features shown in the Figures are merely illustrative of particular embodiments of the disclosure. Accordingly, other embodiments can have other details and features without departing from the spirit and scope of the present disclosure. A person of ordinary skill in the relevant art will therefore understand that the present technology, which includes associated devices, systems, and procedures, may include other embodiments with additional elements or steps, and/or may include other embodiments without several of the features or steps shown and described below with reference to FIGS. 1-16. Furthermore, various embodiments of the disclosure can include structures other than those illustrated in the Figures and are expressly not limited to the structures shown in the Figures.

I. Delivery Systems for Stents Having Drug-Delivery Features and Other Structures and Associated Devices and Methods FIG. 1 is a partially schematic side view of a delivery system 100 for stents having drug-delivery features ("the system 100") in a delivery state (e.g., low-profile or collapsed configuration). In the embodiment illustrated in FIG. 1, the system 100 includes an elongated inner shaft 110 (e.g., a guidewire tube or a guidewire) disposed within an elongated outer shaft 120 (e.g., a catheter) lumen. The system 100 also includes a proximal connector, such as a luer connector 175, coupled to a proximal portion 110*a* of the elongated inner shaft 110. The luer connector 175 may comprise a single piece component or a multi-piece component having two or more components configured to mate together. When configured with two or more components, the luer connector 175 can further be adapted to facilitate insertion of the elongated inner shaft 110 into the elongated outer shaft 120. In addition, when configured with two or more components, the luer connector 175 can be adapted to facilitate flushing of the system 100, such as delivering one or more fluids to at least a portion of the system 100. The inner shaft 110 can be formed as a tubular structure (with or without a slit), such as a coiled tube, a braided tube, a reinforced tube, or a combination thereof, and may be constructed of a polymer material, such as a polyimide. In other embodiments, however, the inner shaft 110 comprises a guidewire and, in such embodiments, the system 100 may optionally include a second guidewire (not shown) laterally disposed within the lumen of the elongated outer shaft 120 or along a portion of an exterior wall of the outer shaft 120. In some embodiments, the outer shaft 120 may also include one or more layers. In these embodiments, for example, the layers of the outer shaft 120 can include an inner layer, an outer layer, a liner, or a combination thereof. Each of the layers can be formed from materials including a polymer, high-density polyethylene (HDPE), polytetrafluoroethylene, silicone, Pebex® (polyether block amide) or a combination thereof. In some embodiments, each of the layers of the outer shaft 120 are formed from the same material. In other embodiments, however, one or more of the layers may be formed from different materials.

In the exploded view of the distal portion 100*b* of the system, a tip 115 (e.g., an atraumatic tip) is disposed on a distal terminal end of the elongated inner shaft (not shown). As illustrated, the tip 115 is adjacent to a distal terminal end of the elongated outer shaft 120. The tip 115 may have the same cross-sectional dimension as the elongated outer shaft (e.g., 5 French), or the tip 115 may have a different cross-sectional dimension. In some embodiments, a distal end 115*b* of the tip 115 is tapered such that the distal end 115*b* has a smaller cross-sectional dimension compared to a proximal end 115*a* of the tip. Distal and/or proximal edges of the tip 115 may be curved/rounded so as to prevent the tip 115 from getting caught (e.g., stuck) on other portions of the system 100 during delivery, positioning, deployment, etc.

The tip 115 can be formed of the same material(s) as the elongated outer shaft 120. In other embodiments, however, the tip 115 can be formed from different material(s) than the outer shaft 120.

The elongated inner shaft 110 and the elongated outer shaft 120 can be sized and shaped for intravascularly accessing a target site (e.g., treatment site) of the patient. In some embodiments, for example, the elongated outer shaft 110 has a length of about 150 cm to about 180 cm and a suitable cross-sectional dimension for positioning within a subject's vasculature. The length of the elongated inner shaft 110 can be a working length, such as a length that can be positioned within a subject's vasculature. In some embodiments, for example, the working length is about 70 cm to about 300 cm, about 150 cm to about 250 cm, or about 70 cm, about 80 cm, about 90 cm, about 100 cm, about 110 cm, about 120 cm, about 130 cm, about 140 cm, about 150 cm, about 160 cm, about 170 cm, about 180 cm, about 190 cm, about 200 cm, about 210 cm, about 220 cm, about 230 cm, about 240 cm, about 250 cm, about 260 cm, about 270 cm, about 280 cm, about 290 cm, or about 300 cm. In other embodiments, the elongated outer shaft 120 has a length of about 130 centimeters (cm) to about 140 cm and a cross-sectional dimension of about 4 French, about 5 French, or about 6 French. The length of the elongated outer shaft 120 can be a working length, such as a length that can be positioned within a subject's vasculature. In some embodiments, the working length is about 50 cm to about 200 cm, about 100 cm to about 150 cm, or about 50 cm, about 60 cm, about 70 cm, about 80 cm, about 90 cm, about 100 cm, about 110 cm, about 120 cm, about 125 cm, about 130 cm, about 135 cm, about 140 cm, about 145 cm, about 150 cm, about 155 cm, about 160 cm, about 170 cm, about 180 cm, about 190 cm, or about 200 cm.

In the exploded view of the proximal portion 100a of the system 100 in FIG. 1, a proximal end 120c of the elongated outer shaft is coupled to an outer shaft hub 140. In the illustrated embodiment, the outer shaft hub 140 is fixedly coupled to the outer shaft 120 (e.g., via bonding). The outer shaft hub 140 can be formed of polycarbonate using various techniques known to those of ordinary skill in the art, such as molding. The system 100 can optionally include a force element 130, such as a strain relief element, directly and fixedly coupled to a distal end of the outer shaft hub 140. In some embodiments, the force element 130 can at least partially cover portion of the proximal portion 120a of the outer shaft. The force element 130 is configured to maintain the guidewire 160, inner shaft 110, and outer shaft 120 in a substantially linear arrangement, for example, by preventing formation of any kinks, folds, turns, collapsed portions, and/or combinations thereof while the system 100 is in the delivery or expanded states. The force element 130 can be formed of a tube, such as shrink tubing molded from one or more flexible materials, including polyurethane and Pebex® (e.g., Pebex® 35D). In other embodiments, however, the proximal end 120c of the outer shaft is directly coupled to the outer shaft hub 140.

The outer shaft hub 140 is further fixedly coupled to a connector 150 (e.g., y-connector) having a lumen extending therethrough (not shown). In particular, a distal end 150b of the connector 150 can be coupled to the outer shaft hub 140 via a mating feature and a receiving feature (not shown). The mating and receiving features can be coupled to the proximal portion of the outer shaft 120 or the distal end 150b of the connector 150. A proximal end 150a of the connector 150 can include a touhy bourst seal configured to secure a position of one or more shafts within the system 100. The connector 150 further includes an outlet port 152 extending radially and/or longitudinally therefrom. The system 100 can optionally include a hemostasis connector 170 coupled to the proximal end 150a of the y-connector 150.

The system 100 is configured to carry a drug-eluting stent (not shown) in a delivery/collapsed state within a distal portion of the elongated outer shaft 120. As described in greater detail below, systems configured in accordance with the present technology can be further configured to carry a non-drug-eluting stent. In some embodiments, the stent can be at least partially ensheathed by the elongated outer shaft 120. The stent can be fixedly or removably coupled to an actuation mechanism (e.g., a stabilizing wire 160) by any suitable process. In some embodiments, the actuation mechanism is integrally formed within a portion of the stent, such as a proximal portion. In other embodiments, a distal portion of the actuation mechanism is welded or attached using a clamp to a proximal portion of the stent. As shown and explained in greater detail with reference to FIG. 3, a visual marker can be located on a proximal portion of the stent, for example, at a location where the actuation mechanism is coupled to the stent. Although the system 100 is illustrated as a delivery system for stents, it will be appreciated that embodiments of the present technology can also include cages, meshes, balloons, membranes, tubular structures, circumferential bodies, expandable elements, expandable membranes, expandable structures, expandable tubular structures, and circumferentially expandable catheter tips with and without guidewire lumens. As described in greater detail with respect to FIGS. 6A-6D, systems configured in accordance with the present technology can be configured for intraluminal delivery through a body lumen (e.g., blood vessel) of the patient to position the stent (not shown) at a desired treatment location within the body lumen.

As noted above, in the embodiment illustrated in FIG. 1 a stabilizing wire 160 is coupled to the stent. The stabilizing wire 160 is slideably disposed within the elongated outer shaft 120 and is sized and shaped to extend distally from the proximal end of the outer shaft and to extend proximally from a proximal end of the outlet port. The stabilizing wire 160 can be formed of plastic, such as high durometer plastic including nylon, polyether ether ketone (PEEK), a metal, a metal alloy, such as nitinol, and/or combinations thereof. The stabilizing wire 160 can be configured to position the stent (not shown) at the desired treatment location (e.g., see vessel 720 of FIG. 7) and to at least generally maintain the position of the stent while the elongated outer shaft 120 is withdrawn as described in greater detail below with reference to FIG. 16.

The stabilizing wire 160 can be sized and shaped to extend proximally from the proximal end of the outlet port when the stent is positioned at the target site. For example, the stabilizing wire 160 can have a length of about 150 cm to about 180 cm and a suitable cross-sectional dimension for positioning within the patient's body lumen. The stabilizing wire 160 can have a working length (i.e., a length that can be positioned within the target body lumen) of about 70 cm to about 300 cm, about 150 cm to about 250 cm, or about 70 cm, about 80 cm, about 90 cm, about 100 cm, about 110 cm, about 120 cm, about 130 cm, about 140 cm, about 150 cm, about 160 cm, about 170 cm, about 180 cm, about 190 cm, about 200 cm, about 210 cm, about 220 cm, about 230 cm, about 240 cm, about 250 cm, about 260 cm, about 270 cm, about 280 cm, about 290 cm, or about 300 cm.

Figure 2A:
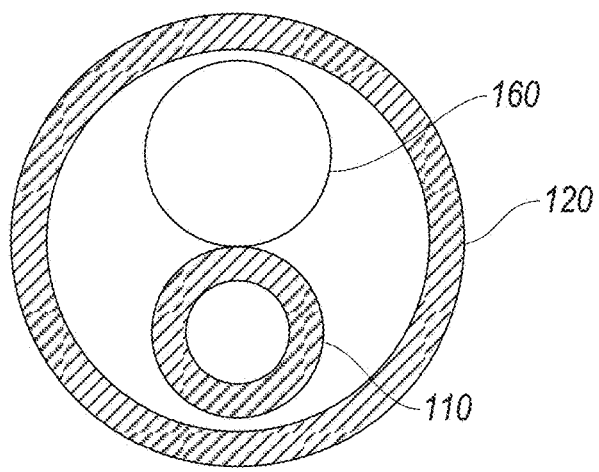

FIGS. 2A-2F are cross-sectional views of various configurations of the region of the drug delivery system 100 of FIG. 1 taken along line 2-2. As illustrated in FIG. 2A, the elongated inner shaft 110 (e.g., guidewire tubing and/or guidewire) and the stabilizing wire 160 are least partially disposed within a lumen of the elongated outer shaft 120. In some embodiments, the outer shaft 120, the inner shaft 110, and the stabilizing wire 160 each have a circular cross-sectional shape. In other embodiments, however, the outer shaft 120, the inner shaft 110, and the stabilizing wire 160 can have other cross-sectional shapes, such as an ovoid shape, a "C" shape, a rectangular shape, a triangular shape, or the like.

The stabilizing wire 160 and the inner shaft 110 can be positioned within the lumen of the outer shaft 120 in any configuration such as anteriorly and posteriorly as illustrated, or medially and laterally. Furthermore, the stabilizing wire 160 and the inner shaft 110 can be positioned in the lumen of the outer shaft 120 with respect to one another as illustrated, or the stabilizing wire 160 and the inner shaft 110 can be positioned in an opposite arrangement, with the stabilizing wire 160 positioned where the inner shaft 110 is illustrated and vice versa. In further embodiments, the drug delivery system of FIG. 4 may have any of the configurations and/or arrangements illustrated in FIG. 2A or described herein with reference thereto.

Figure 2B:
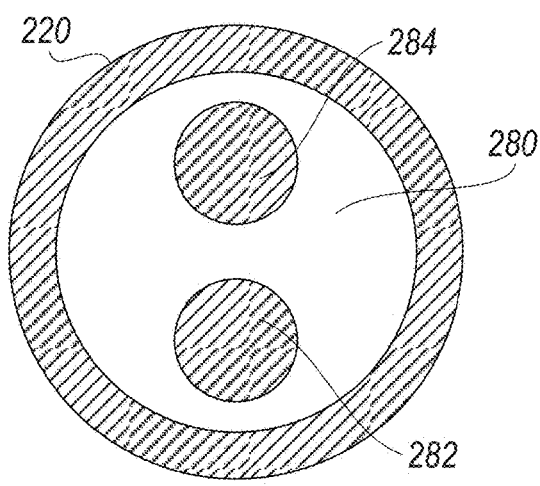
Figure 2C:
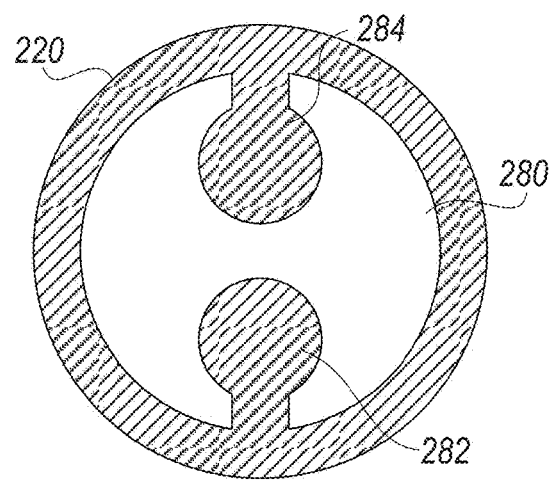

As illustrated in FIGS. 2B-2F, systems configured in accordance with embodiments of the present technology, can optionally include a pusher shaft 280 rather than the stabilizing wire 160. When systems are configured in accordance with these embodiments, the pusher shaft 280 is at least partially disposed within the lumen of the outer shaft 120. In these embodiments, the pusher shaft 280 includes a first pusher shaft lumen 282 and, optionally, a second pusher shaft lumen 284, each having a circular cross-sectional shape and ensheathed by the pusher shaft 280 (FIGS. 2B-2D). In other embodiments, the first pusher shaft lumen 282 and the second pusher shaft lumen 284 have a cross-sectional "C" shape, where the pusher shaft lumens 282 and 284 are partially sheathed by the pusher shaft 280 (FIGS. 2B-2D). The "C" shaped pusher shaft lumens 282 and 284 are configured to allow rapid removal of a shaft carried therein, such as the inner shaft 110 and/or a stent pull wire shaft (not shown), for example, by longitudinally advancing at least a portion of either shaft through the "C" shaped opening. Moreover, in some configurations, rather than having the inner shaft lumen 284, the pusher shaft 280 may have a semi-circular cross-sectional shape (FIGS. 2E and 2F). In these configurations, a stent pull wire 118 is carried by the outer shaft 220. The position of the stent pull wire 228 is at least partially maintained in the outer shaft lumen 266 by the shape of the pusher shaft 280. In other embodiments, the first and second pusher shaft lumens 282 and 284 can have any number of other suitable shapes known to one of ordinary skill in the art. In further embodiments, system 100 illustrated in FIG. 1 and system 400 illustrated in FIG. 4 and discussed below with reference to FIG. 4 may have any of the configurations illustrated in FIGS. 2B-2F or described with reference thereto.

FIG. 3 is a partially schematic side view of a distal portion 100b of the drug delivery system of FIG. 1 in a deployed state. In the illustrated embodiment, a stent 190 is fixedly coupled to the stabilizing wire 160 and has been unsheathed from the distal portion 120b of the elongated outer shaft. A proximal visualization marker 192 is disposed on the stabilizing wire 160 near a proximal portion of the stent 190 and distal visualization markers 197 are disposed on a distal end 190c of the stent. In some embodiments, the proximal visualization marker 192 and/or the distal visualization marker 197 may be disposed on the stabilizing wire 160. The visualization markers 192/197 can be formed from any material that can be visualized while the stent 190 is intravascularly positioned (e.g., within a target blood vessel). In one embodiment, for example, the visualization markers 192/197 are radiopaque markers. The tip 115 is disposed on a terminal end 110c of the elongated inner shaft (e.g., the guidewire) and can ensheath the terminal end 110c extending proximally along the distal portion 110b and/or distally from the terminal end 110c. The inner shaft 110 (FIG. 1) extends distally from the distal end of the outer shaft, through a lumen of the stent 190, and, optionally, extends distally from the distal end of the stent. In the deployed configuration, drug-delivery features 194 extend radially from a longitudinal axis of the stent 190.

Figure 4:
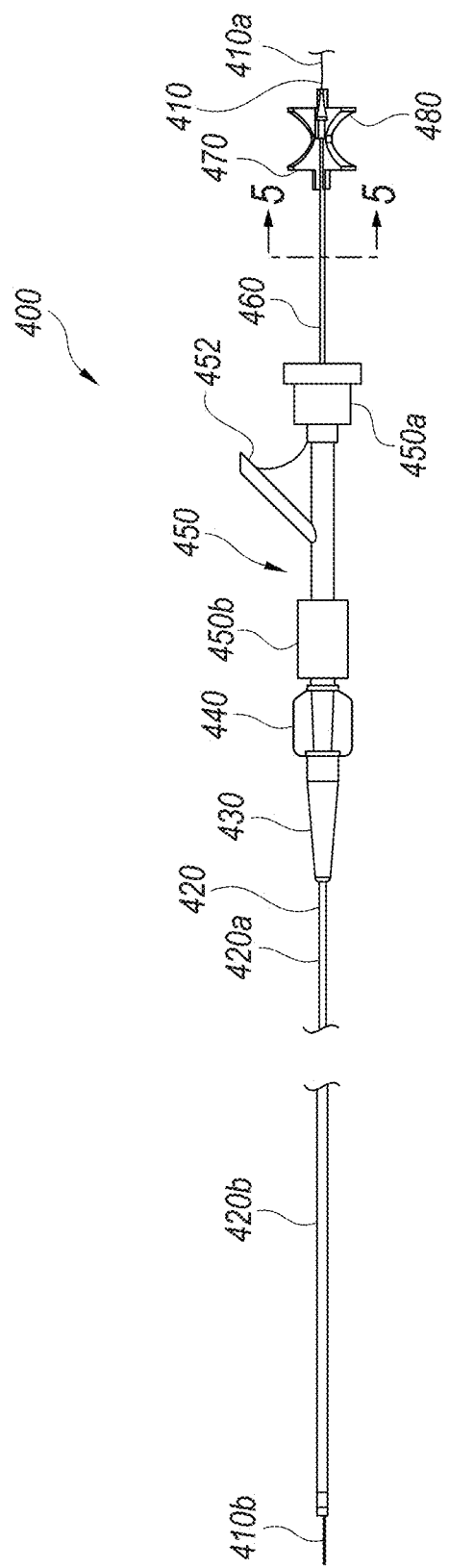
FIG. 4 is a partially schematic side view of another delivery system in a delivery state (e.g., low-profile or collapsed configuration) configured in accordance with an embodiment of the present technology.

FIG. 4 is a partially schematic side view of a delivery system 400 for stents ("the system 400") in a delivery state (e.g., low-profile or collapsed configuration) configured in accordance with an embodiment of the present technology. In the embodiment illustrated in FIG. 4, the system 400 includes, for example, an elongated inner shaft 410 (e.g., a guidewire tube) disposed within an elongated outer shaft 420 (e.g., a catheter) lumen. The inner shaft 410 and outer shaft 420 include proximal portion 410a and 420a, respectively, and distal portions 410b and 420b, respectively. The inner shaft 410 can be formed as a tube (with or without a slit) and may be constructed of a polymer material, such as a polyimide. In other embodiments, the inner shaft 410 is a guidewire and in these embodiments, the system 400 may optionally include a second guidewire. The outer shaft 420 can be formed and have the properties of outer shaft 120 explained above with reference to FIG. 1.

As illustrated in FIG. 4, a proximal end of the elongated outer shaft 420 is coupled to an outer shaft hub 440. The outer shaft hub 440 can be fixedly coupled to the outer shaft 420 (e.g., by bonding). The outer shaft hub 440 can be formed of polycarbonate using any number of techniques known to one of ordinary skill in the art, such as molding. The system 400 can optionally include a force element 430, such as a strain relief element, directly and fixedly coupled to a distal end of the outer shaft hub 440. The force element 430 can be formed of a tube, such as shrink tubing molded from one or more flexible materials, including polyurethane and Pebex® (e.g., Pebex® 35D). The outer shaft hub 440 also is fixedly coupled to a connector 450 (e.g., y-connector). In particular, a distal end 450b of the connector 450 can be coupled to the outer shaft hub 440 via a mating feature and a receiving feature (not shown). The mating and receiving features can be coupled to the proximal portion of the outer shaft 420 or the distal end 450b of the connector 450. A proximal end 450a of the connector 450 can include a toughy bourst seal configured to secure a position of one or more shafts within the system 400. In some embodiments, the connector 450 may also include an outlet port 452 extending radially and/or longitudinally therefrom.

The system 400 can further include a pusher shaft 280 disposed within the connector lumen, which extends distally into the outer shaft lumen and proximally from the proximal end 450a of the connector 450. The pusher shaft 280 can be formed of plastic, such as high durometer plastic including nylon, polyether ether ketone (PEEK), and/or combinations thereof. The toughy bourst seal at the proximal portion 450a of the connector 450 can be configured fixedly position (e.g., secure) the pusher shaft 280 at a desired location (e.g., vessel wall, see 520 of FIG. 5). In this embodiment, the pusher shaft 280 is fixedly coupled to a pusher shaft hub 480 at a proximal portion of the pusher shaft. In other embodiments, however, the pusher shaft hub 480 can be removably coupled to the pusher shaft 280. As discussed in greater detail with respect to FIG. 2 above, the pusher shaft 280 can include two or more pusher shaft lumens, channels, or a combination thereof extending therethrough, such as a first pusher shaft lumen configured to carry a guidewire or guidewire tube (e.g., inner shaft 410) and a second pusher shaft lumen configured to carry a wire, such as a stent pull wire (not shown).

In some embodiments, the system 400 may further include a stent pull wire hub 470 coupled to a proximal portion of the stent pull wire. If coupled to the system 400, the stent pull wire hub 470 and the pusher shaft hub 480 can each include a mating feature or a receiving feature (neither are shown) configured to engage with one another and removeably couple the stent pull wire hub 470 to the pusher shaft hub 480. Both the stent pull wire hub 470 and the pusher shaft hub 480 can be molded or machined from any suitable material.

The system 400 is configured to carry a stent (not shown) in a delivery/collapsed state within a distal portion 420b of the elongated outer shaft 420 and coupled to an actuation mechanism (e.g., stent pull wire). Although the system 400 is illustrated as a delivery system for stents, it will be appreciated that embodiments of the present technology can also include cages, meshes, balloons, membranes, tubular structures, circumferential bodies, expandable elements, expandable membranes, expandable structures, expandable tubular structures, and circumferentially expandable catheter tips with and without guidewire lumens. As described in greater detail with respect to FIGS. 4A-4D, the system 400 is configured for intravascular delivery through a body lumen (e.g., a vessel lumen) to position the stent (not shown) at a desired treatment location.

Figure 5:
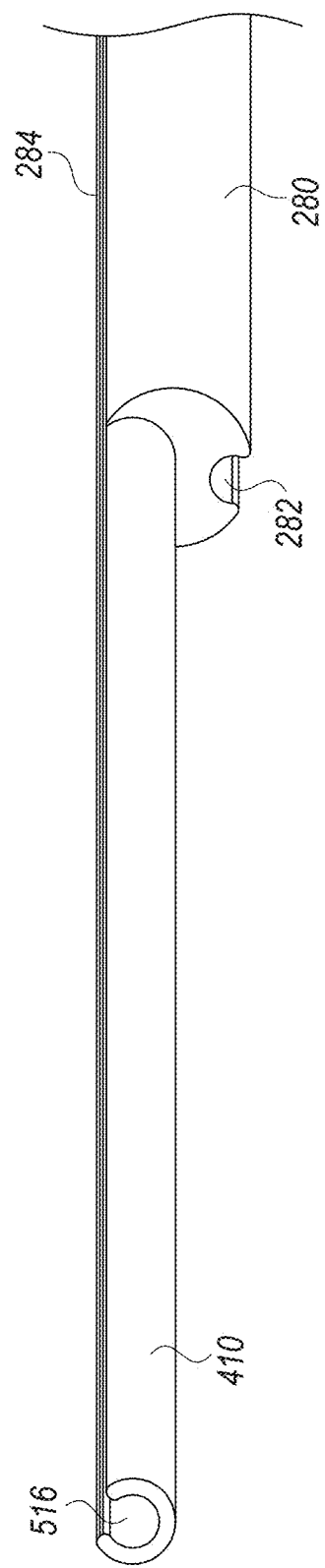
FIG. 5 is an isometric side view of the region of the delivery system of FIG. 4 taken along line 5-5.

FIG. 5 is an isometric side view of the region of the system 400 of FIG. 4 taken along line 5-5. In the embodiment shown in FIG. 5, the pusher shaft 280 includes a first pusher shaft channel 284 and a second pusher shaft channel 282. As shown, a portion of the inner shaft 410 is disposed within the first pusher shaft channel 284 (e.g., inner shaft channel). In this embodiment, the inner shaft 410 has a guidewire channel 516 configured to carry the guidewire (not shown). The second pusher shaft channel 282 (e.g., stent pull channel lumen) is configured to carry the stent pull wire (not shown). The first pusher shaft channel 284 and the second pusher shaft channel 282 can each have a number of arrangements and orientations within the pusher shaft 280 (FIGS. 2B-2F). These arrangements and orientations are configured to facilitate release of shaft carried therein, such as the inner shaft 410 and/or a stent pull wire (not shown), and engagement with a different shaft (e.g., catheter exchange).

Figure 6A:
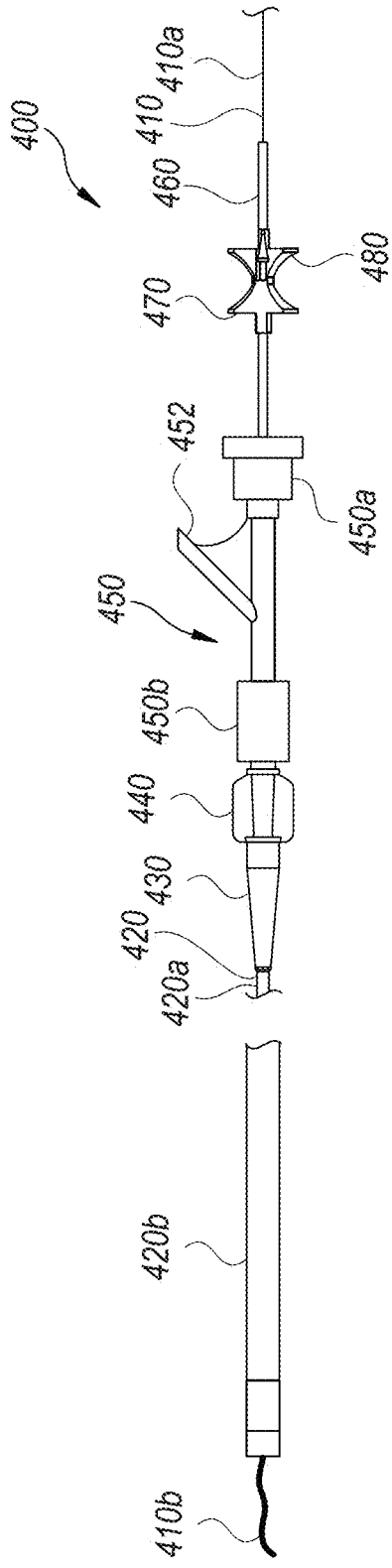
FIGS. 6A-6D are partially schematic side views of the delivery system of FIG. 4 in various stages of the delivery procedure in accordance with an embodiment of the present technology.

FIGS. 6A-6D are partially schematic side views of the system 400 in various stages of the delivery procedure in accordance with an embodiment of the present technology. As illustrated in FIG. 6A, the system 400 is initially configured in a low-profile delivery state. In this initial arrangement, a distal region of the system 400, including the distal portion 410b of the inner shaft 410 and the distal portion 420b of the outer shaft 420, is configured to be advanced distally through a body lumen (e.g., vessel lumen, such as a femoral artery), along a guidewire to the desired location. In some embodiments, at least a portion of the system 400 may also be delivered within a suitably sized guide sheath (e.g., 5 French or 6 French).

Figure 6B:
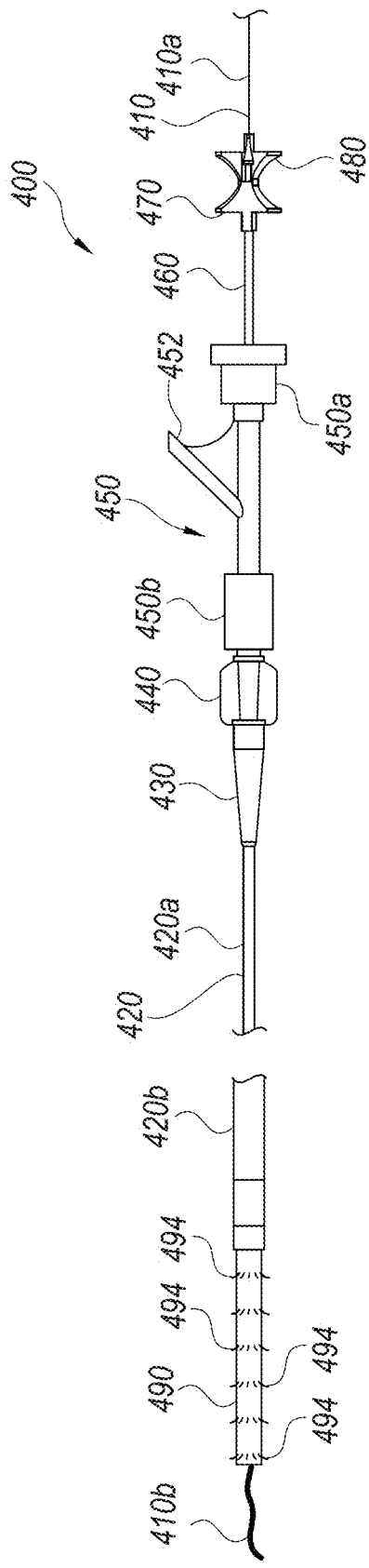

Referring next to FIG. 6B, once the distal region of the system 400 is positioned at a desired location, the outer shaft 420 is configured to be at least partially proximally retracted by retracting the outer shaft hub 440. Once the outer shaft 420 is partially retracted, a portion of the stent 490 are unsheathed and drug-delivery features 494 are configured to radially expand outward from the system 400. The pusher shaft 280, carried by the outer shaft 420, is configured engage with the proximal end 490a of the stent and distally advance and release the stent 490. As described above with reference to FIGS. 2B-2F, the pusher shaft 280 is configured to carry the inner shaft 410 and the stent pull wire 182. In this embodiment, the pusher shaft 280 is configured to be distally advanced before, during, or after the outer shaft 420 is partially proximally retracted.

Figure 6C:
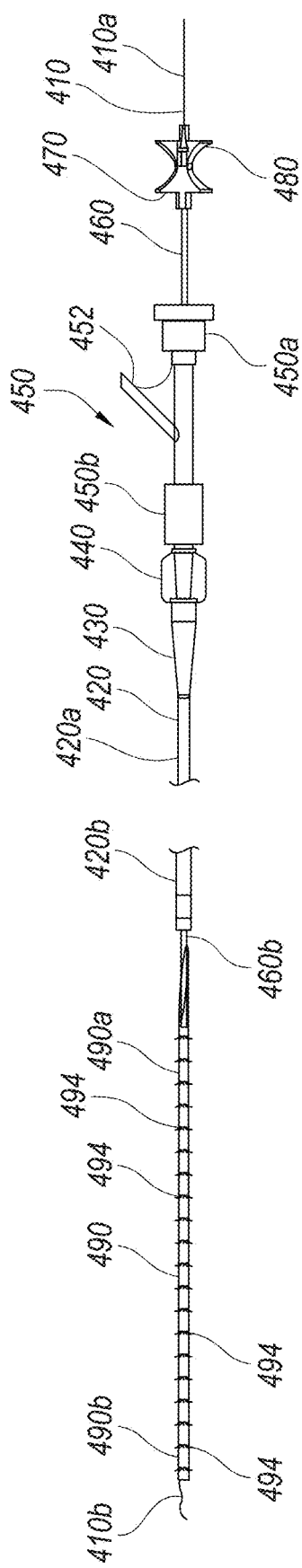

As illustrated in FIG. 6C, the outer shaft 420 has been retracted and the stent 490 is unsheathed. In this arrangement, the stent 490 is configured to be distally advanced by the pusher shaft 280 and, after advancement, the pusher shaft 280 is configured to be fixed, for example, by being held or pinned by the pusher shaft hub 480 to maintain a position of the stent 490.

Figure 6D:
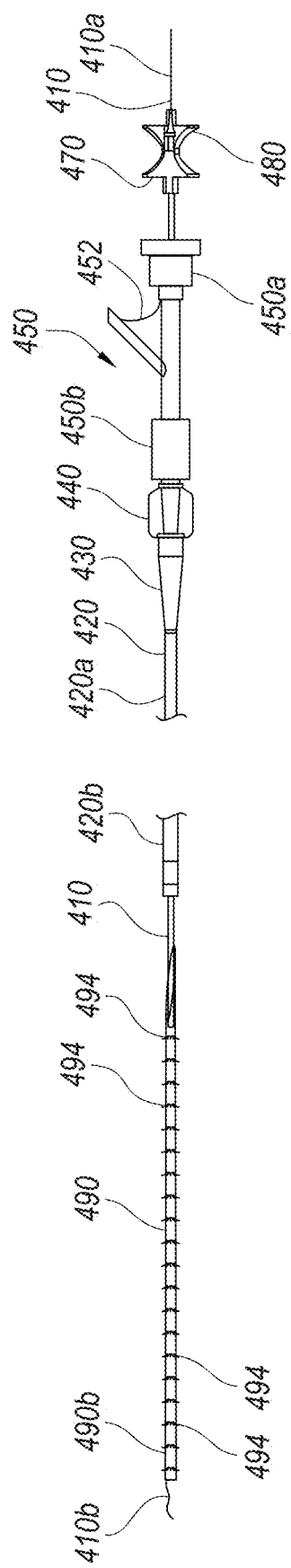

Referring next to FIG. 6D, the pusher shaft 280 is further configured to be removed by proximally advancing the pusher shaft hub 480 once the stent 490 is in position. In the embodiment shown in FIG. 6D, after the pusher shaft 280 has been removed, system 400 is configured for insertion of a balloon (not shown, see balloon 840 of FIG. 8A) into a proximal portion 420a of the outer shaft 420 and distal advancement of the balloon to the distal portion 420b of the outer shaft 420.

As described further below, the expandable stent 490 includes a plurality of drug-delivery features 494 carried by the stent 490. In some embodiments, the plurality of drug-delivery features 494 are configured to radially expand after the stent 490 has been unsheathed from the outer shaft 420. Moreover, several embodiments can be designed for application of a drug onto the stent or the drug-delivery features that are configured to receive the drug and release the drug once the stent is expanded at the desired location (e.g., target site, treatment site). In some embodiments, the outer shaft 420 may include an inner layer configured to prevent debris released from the drug-delivery features 494 of the stent 490 from entering the lumen of the outer shaft.

Figure 7:
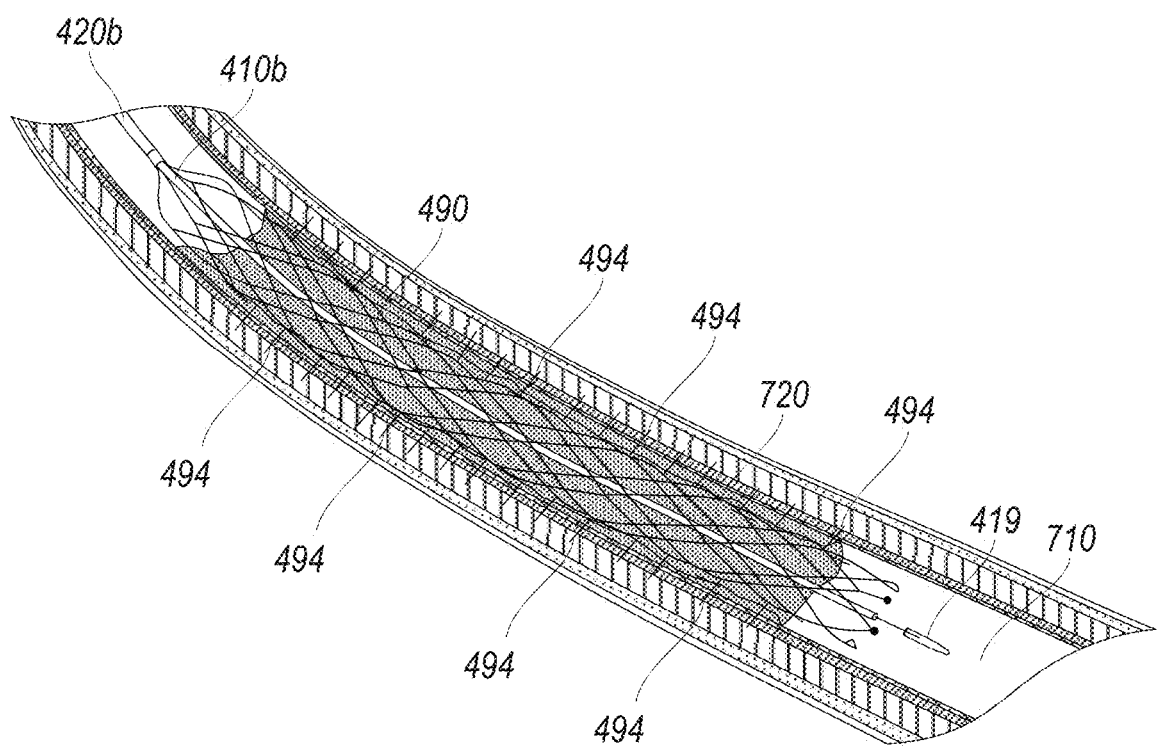
FIG. 7 is a partially schematic side view of a region of the delivery system of FIG. 4 in the delivery state within a body lumen and configured in accordance with an embodiment of the present technology.

The system 400, various configurations of the system 400, and other systems described herein can be used to deliver, position, deploy, and/or recapture the stent 190, other stents, or other suitable elements according to procedures and methods described herein as well as those known to persons of ordinary skill in the art. For example, FIG. 7 is a partially schematic side view of a distal portion of the system 400 in the delivery state in accordance with an embodiment of the present technology. As illustrated in FIG. 7, the system 400 is in a delivery state within a body lumen 710 (e.g., a blood vessel) of a human patient. In this embodiment, system 400 is configured for intraluminal (e.g., intravascular) delivery through the blood vessel, (e.g., femoral artery) of a human patient. The femoral artery is accessed by introducing a sheath (e.g., 5F or 6F) and guidewire into the lumen of the femoral artery. The system 400 is delivered into the body lumen by tracking the distal portion 410b of the inner sheath over the guidewire and distally advancing the system 400 to a desired location 720 within the vessel. In many embodiments, an angioplasty procedure is performed at the desired location 720 before the system 400 is advanced to the desired location 720. In these embodiments, the guidewire can be the same guidewire that was used for the angioplasty.

Once the system 400 is positioned at the desired location 720, the distal portion 420b of the outer sheath is proximally retracted to unsheath the stent 490. In the illustrated embodiment, the body of the stent 490 is at least partially expanded when unsheathed and the drug-delivery features 494 are collapsed. However, the drug-delivery features 494 can be configured to expand once the distal portion 420b of the outer sheath is retracted. In other embodiments, the stabilizing wire (not shown) can be distally advanced and fixed, such as held or pinned, or fixed at the desired location to position the stent before, during, and/or after the outer sheath is proximally retracted to deploy the stent. As illustrated, the distal tip 419 of system 400 is positioned distally from the distal end of the stent and the inner shaft 410 remains positioned within at least a portion of the lumen of the stent 190.

Figure 8A:
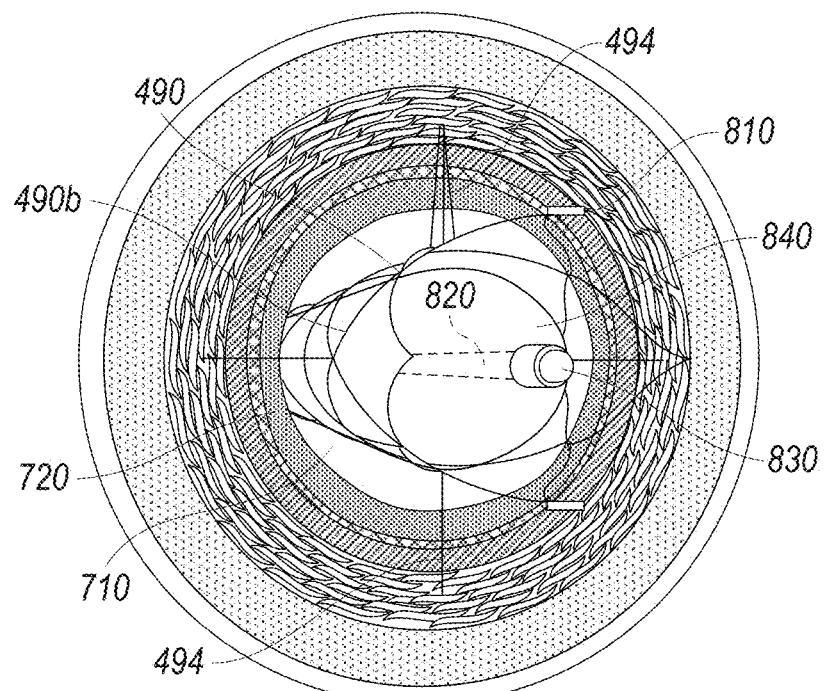
FIGS. 8A and 8B are cross-sectional views of a region of the delivery system of FIG. 4 in a deployed state (FIG. 8A) and a drug-eluting expandable structure in an expanded state (FIG. 8B) within a body lumen and configured in accordance with an embodiment of the present technology.
Figure 8B:
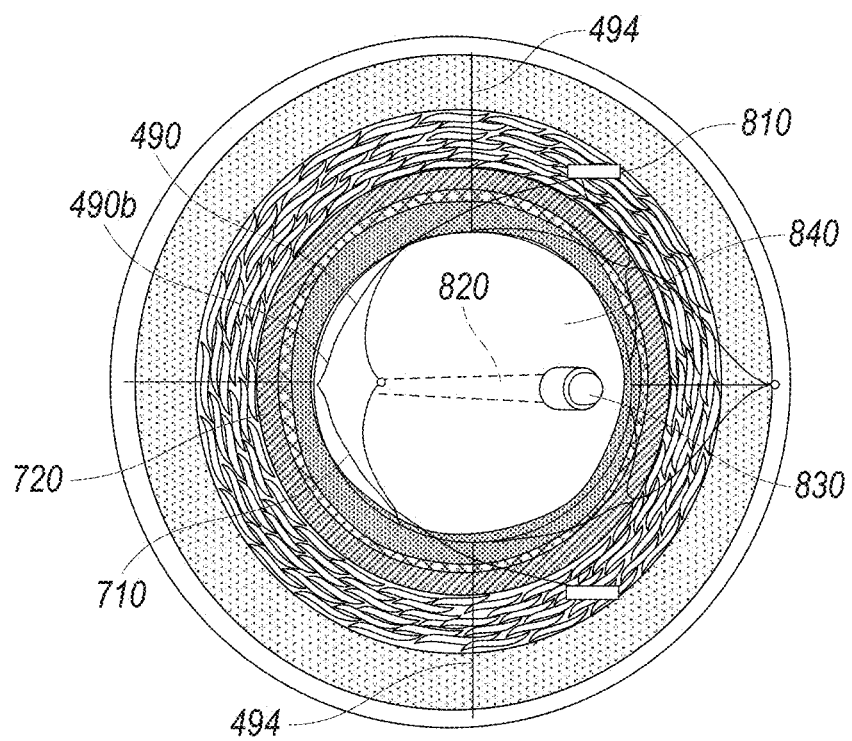

In the deployed state, the drug-delivery features 494 of the stent 490 are configured to expand radially and are further configured to pierce the lumen wall at the desired location once the deployed stent 490 is expanded into contact with the vessel wall (see FIGS. 8A and 8B). As will be explained in greater detail below, stents and other expandable structures can be configured to at least partially self-expand, such as expanding outwardly from the collapsed/delivery state to the deployed and/or expanded state when the stents and other expandable structures are at least partially unsheathed from the outer shaft. In some embodiments, stents and other expandable structures are configured to expand when operably coupled with an expandable element or mechanism, such as a balloon. In additional embodiments, self-expanding stents and other structures are configured to further expand when coupled to the expansion mechanism. Regardless of whether the stents and other expandable structures are self-expanding or expand when coupled to the expandable element, the stents and others expandable structures can be configured to expand radially (symmetrically or asymmetrically). In some embodiments, the at least partially expanded stents and other expandable structures can be configured to position at least some of the drug-delivery features perpendicular to the vessel wall.

In the embodiment illustrated in FIGS. 8A and 8B, the system 400 is configured for insertion of a balloon 840 coupled to an elongated shaft, such as a wire into a stent lumen. (see elongated shaft 820 of FIGS. 8A and 8B) The balloon 840 is further configured to be positioned within the stent lumen and expanded therein to further expand the stent 490 between the delivery state and the expanded, deployed state. In some embodiments, the balloon 840 can be coated with a drug-delivery coating and a drug, such as the coatings and drugs described herein. As further discussed elsewhere herein, the stent 490 can be operatively coupled to an actuation mechanism, such as a mechanical actuation mechanism (e.g., stabilizing wire, stent pull wire, pusher shaft, or a combination thereof), configured to position, expand, retract, re-position, and/or remove the stent 490 from the body lumen.

FIG. 8A, is a cross-sectional view of a region of the system 400 in the deployed state within the body lumen in accordance with an embodiment of the present technology. In the embodiment illustrated in FIG. 8A, the stent 490 is expanded within the vessel 720 by a balloon 840. To expand the deployed stent 490, the balloon 840 is coupled to elongated shaft 820 and distally advanced into a lumen of the deployed stent 490 until a distal tip 830 of the elongated shaft 820 is positioned near a distal end 490b of the deployed stent 490. As illustrated, the distal end 490b of the stent 490 includes radiopaque markers 810. However, in other embodiments, the radiopaque markers 810 may be located elsewhere in the system 400, or may be omitted from the system 400.

FIG. 8B is a cross-sectional view of a portion of the system 400 in a deployed state with the stent 490 having drug-delivery features 494 expanded within and piercing a portion of the vessel wall. As illustrated in FIG. 8B, the balloon 840 is deployed and radially expanded to engage with and further expand the stent 490 into contact with the lumen vessel. When the stent 490 is expanded, the drug-delivery features 494 penetrate further into the wall.

Figure 9:
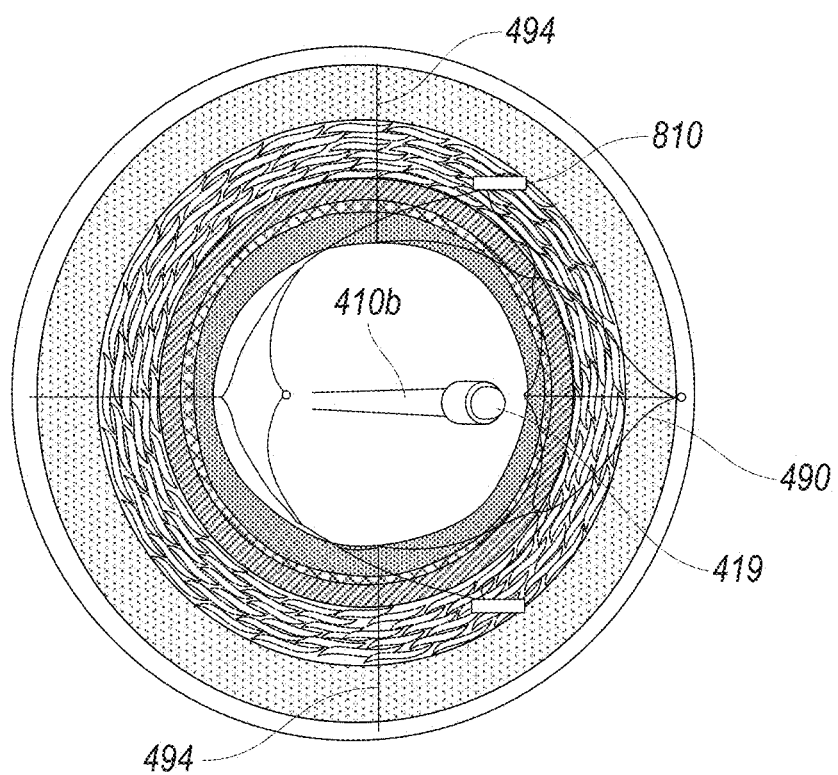
FIG. 9 is a cross-sectional view of the a region of the delivery system of FIG. 4 in a treatment state and configured in accordance with an embodiment of the present technology.

FIG. 9 is a cross-sectional view of the system 400 in a treatment state in accordance with an embodiment of the present technology. In the treatment state, the balloon 840 (FIG. 8A) has been deflated, proximally retracted along the inner shaft 410, and removed from the body lumen. As illustrated, the distal portion 410b of the inner shaft 410 remains in the body lumen. Following removal of the balloon 840, the stent 490 remains expanded into contact with the lumen wall and the drug-delivery features 494 remain penetrated into the wall. Any drugs carried by the drug-delivery features 494 are at least partially released into the body lumen wall at the treatment state. In other embodiments, the stent 490 can be affixed to the balloon 840, such as by crimping the stent 490 to at least partially surround the balloon 840, and can be expanded and collapsed by inflating and deflating the balloon 840, respectively.

Figure 10:
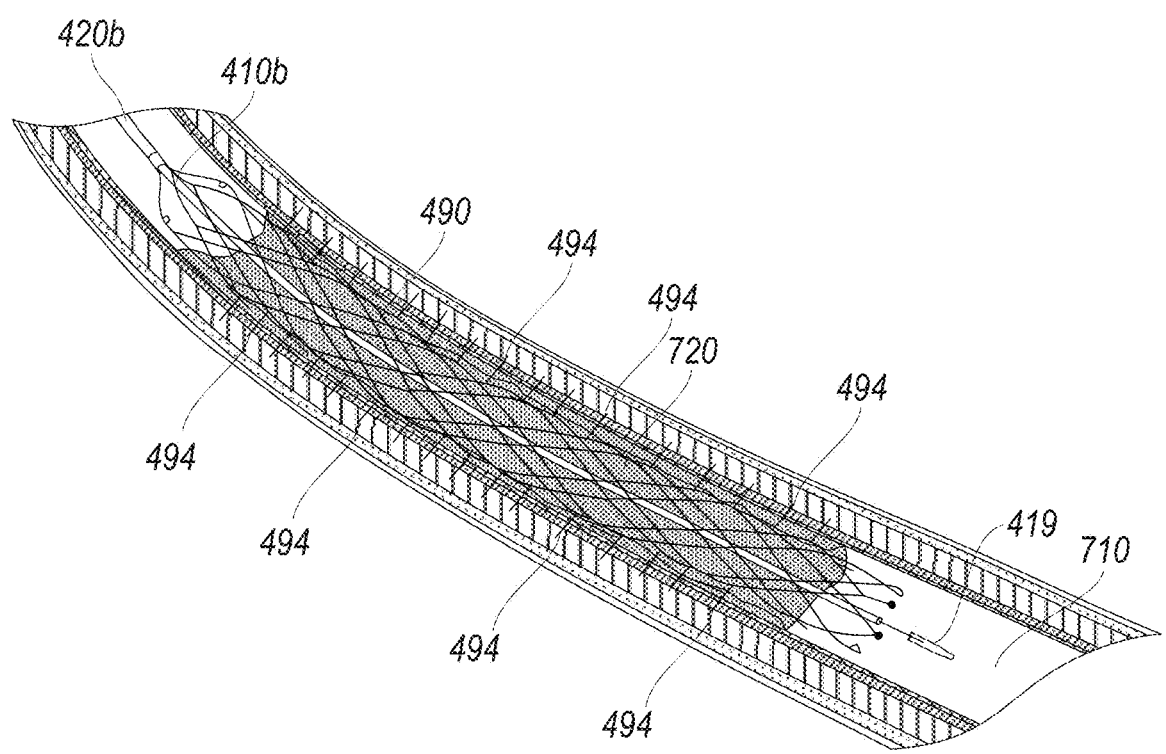
FIG. 10 is a partially schematic side view of a region of the delivery system of FIG. 4 in a removal state configured in accordance with an embodiment of the present technology.

In some embodiments, certain elements of the system 400 are further removed from the body lumen after the stent 490 has been expanded. For example, FIG. 10 is a partially schematic side view of a region of the system 400 in a removal state in accordance with an embodiment of the present technology. As illustrated in FIG. 10, the stent 490 remains expanded into contact with the wall of the vessel 720 and as the distal portions of the inner shaft 410 and outer shaft 420 are proximally retracted. Retrieval systems and associated devices and methods are discussed further below with reference to FIGS. 11, 12 and 16.

Figure 11:
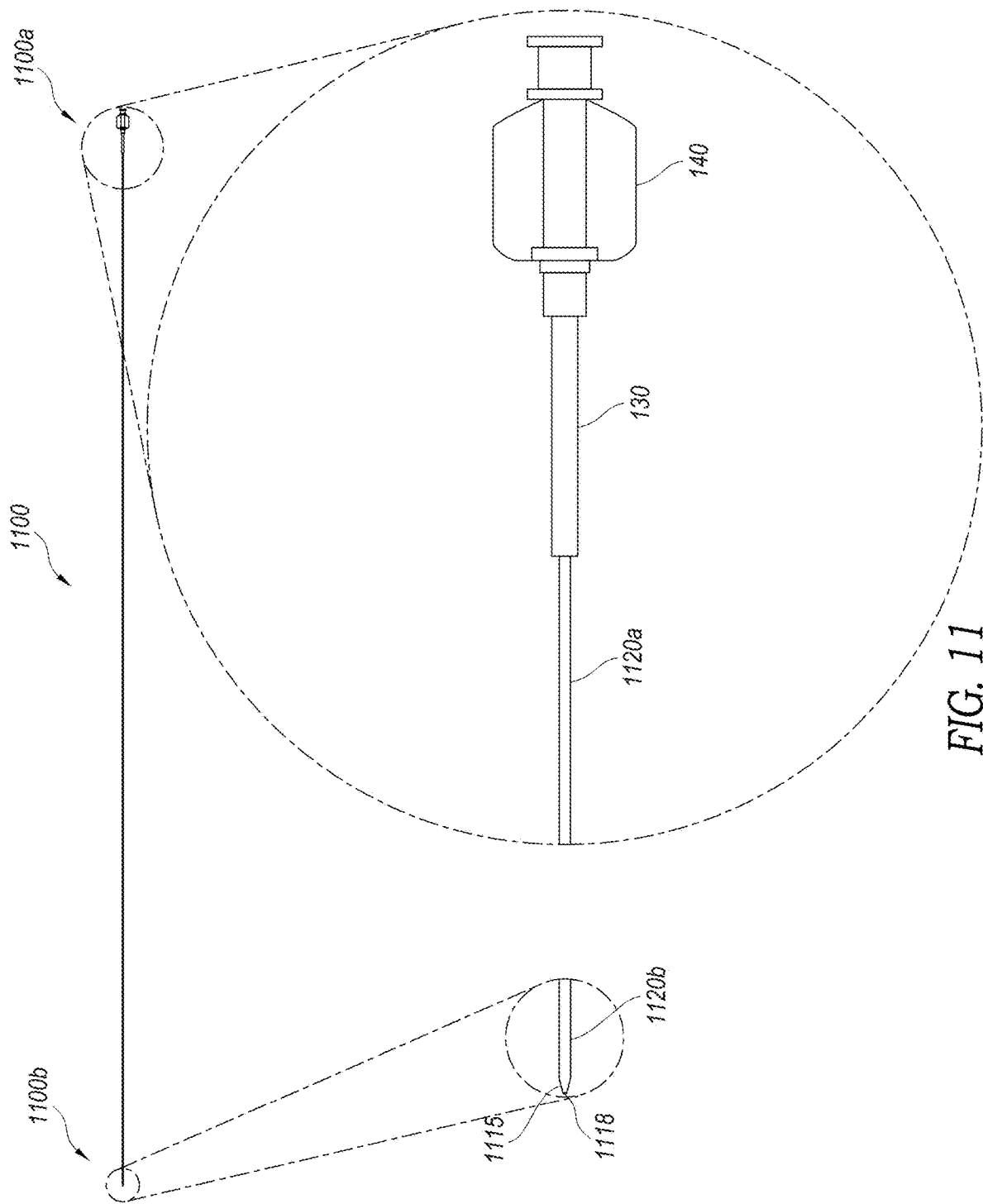
FIG. 11 is a partially schematic side view of a retrieval system configured in accordance with an embodiment of the present technology.

FIG. 11 is a partially schematic side view of a retrieval system ("the system 1100") configured in accordance with an embodiment of the present technology. In the embodiment illustrated in FIG. 11, the system 1100 includes an elongated outer shaft 1120 having a tip 1115 at a distal portion 1120b of the outer shaft (see exploded view of the distal portion 1100b). In some embodiments, the tip 1115 is tapered such that the distal end has a smaller cross-sectional dimension compared to a proximal end. Further, at least a portion of the tip 1115 can have the same cross-sectional dimension as the elongated outer shaft 1120 (e.g., 5 French). The tip 1115 is configured to engage with a proximal portion of the stent (not shown). Distal and/or proximal edges of the tip 1115 can be rounded so as to prevent the tip 1115 from getting caught (e.g., stuck) on other portions of the system 1100, during retrieval of a stent, or any other uses that the system 1100 can be configured for.

In the embodiment illustrated in FIG. 11, the tip 1115 is continuous with the outer shaft 1120. In other embodiments, however, the tip 1115 can be a discrete element coupled to the distal end of the outer shaft. The tip 1115 can be formed of the same material as the elongated outer shaft 1120. In other embodiments, the tip 1115 can be formed from a different material than the outer shaft 1120.

The tip 1115 includes a channel (not shown) fluidly coupled to an opening 1118 at a distal end of the tip and a lumen of the outer shaft (not shown). The channel is configured to carry at least a portion of the inner shaft 110, a guidewire, and/or the stabilizing wire 160 discussed above with reference to FIG. 1. The distal end of the tip is configured to engage with at least a portion of the expanded stent 190 and, once engaged, the tip 1115 is configured to collapse the expanded stent 190 as the outer shaft 1120 is advanced to resheath at least a portion of the collapsed stent 190. As explained in greater detail below, the outer shaft 1120 is configured to at least partially surround a portion of the stabilizing wire 160 (and optionally a guidewire) while the stent 190 is held in position at the target location, collapsed, and at least partially ensheathed. The drug-delivery features 194 can be configured to collapse toward the frame 193 of the stent. Alternatively, the drug-delivery features may be adapted to remain at least partially penetrated into a portion of the lumen wall for a period of time (short-term, such as 1, 2, 5, 10, 15 minutes, 20 minutes, etc.; long-term, such as 1 hour, 2 hours, 3 hours, 6 hours, 12 hours, 24 hours, 48 hours, etc.).

As illustrated in the exploded view of the proximal portion 1110a, the system 1100 further includes force element 130 and the outer shaft hub 140 explained above with reference to FIG. 1 coupled to a proximal portion 1120a of the elongated outer shaft 1120. Similar to the outer shaft 120 of FIG. 1, outer shaft 1120 may also include one or more layers. In these embodiments, for example, the layers of the outer shaft 1120 can include an inner layer, an outer layer, a liner, or a combination thereof. Each of the layers can be formed from materials including, for example, a polymer, high-density polyethylene (HDPE), polytetrafluoroethylene, silicone, Pebex® (polyether block amide) or a combination thereof. In some embodiments, each of the layers of the outer shaft 1120 are formed from the same material. In other embodiments, however, one or more of the layers may be formed from different materials.

The elongated outer shaft 1120 can be sized and shaped for intravascularly accessing a target site within the patient. For example, the elongated outer shaft 1120 has a length of about 130 cm to about 140 cm and a cross-sectional dimension of about 4 French, about 5 French, or about 6 French. The length of the elongated outer shaft 1120 can be a working length (i.e., a length that can be positioned within a subject's vasculature). In some embodiments, for example, the working length is about 50 cm to about 200 cm, about 100 cm to about 150 cm, or about 50 cm, about 60 cm, about 70 cm, about 80 cm, about 90 cm, about 100 cm, about 110 cm, about 120 cm, about 125 cm, about 130 cm, about 135 cm, about 140 cm, about 145 cm, about 150 cm, about 155 cm, about 160 cm, about 170 cm, about 180 cm, about 190 cm, or about 200 cm.

In other embodiments, stents may be collapsed and removed from the body lumen after a drug-delivery procedure, such as stent 490, using the delivery system illustrated in FIG. 4 in a removal configuration. For example, FIGS. 12A-12C are partially schematic side views of the delivery system in a retrieval configuration illustrating various stages of the partially retracted state in accordance with an embodiment of the present technology. As illustrated in FIG. 12A, the stent 490 and drug-delivery features 494 are collapsed toward the distal portion 420b of the outer shaft 420 and engaged with the distal tip of the pusher shaft 280. FIG. 12B illustrates the distal portion 420b of the outer shaft 420 partially resheathing the collapsed stent 490. To re-sheath or partially re-sheath the stent 490, the outer shaft hub 440 can be distally advanced toward the collapsed stent 490 and/or the stent pull wire hub 470 can be proximally retracted as illustrated in FIG. 12C. During re-sheathing, the drug-delivery features 494 can remain pierced into the wall of the body lumen or can be radially retracted/collapsed toward the frame 493 for removal.

Additionally, several embodiments of the present technology can provide for detachment of a stent or other structure including the drug-delivery features within the body lumen. For example, in several embodiments, a wire or attachment member can release the stent via mechanical, thermal, electrical or other means. In some embodiments, the stent can be operatively coupled to a circular or non-circular longitudinal member configured to release and/or recapture the stent in the systems described herein. The member can be coupled, either directly or indirectly, to the frame of the stent. In some of these embodiments, the stent or other structure can be designed for permanent placement within a patient.

II. Stents and Other Structures, Drug-Delivery Features, and Associated Systems and Methods FIG. 13 is a partially schematic side view of a drug-eluting expandable structure (e.g., stent) 1300 having drug-delivery features in the deployed state within a body lumen and configured in accordance with an embodiment of the present technology. The stent 1300 includes a plurality of struts 1310 forming a radially expandable cylindrical frame 1330 and members engaging with and extending between two or more rows of struts 1310. The drug-delivery features 1350 are integrally formed portions of the struts 1310, disposed across at least a portion of an outer dimension of the stent 1300, and extending radially outward away from the stent 1300 toward the target portion of the body lumen. As illustrated, the struts 1310 of the expanded stent 1300 are in apposition with the walls of the body lumen 520. In some embodiments, the stent 1300 is a self-expanding structure, or a partially self-expanding structure. In other embodiments, the stent 1300 can be coupled to a balloon 840 (see FIGS. 7-9), or other suitable techniques and/or structures known to those of skill in the art may be used, to transform the stent 1300 from the low-profile delivery state to the deployed and/or expanded state shown in FIGS. 7-9.

The frame 1330, struts 1313, and/or drug-delivery features 1350 can be composed of or formed from a variety materials including, e.g., nitinol, cobalt chromium, stainless steel, any of a variety of other metals or metal alloys, or a combination thereof. The frame 1330, struts 1313, and/or drug-delivery features 1350 may also be composed of or formed from bioresorbable biodegradable, nanoporous or non-bioresorbable, non-biodegradable, non-nanopourous materials including, e.g., one or more polymers, nitinol, plastic materials, etc., or a combination thereof. In some embodiments, the frame 1330 and the struts 1392 can be formed from a bioresorbable material and the drug-delivery features 1350 can be formed from a non-bioresorbable material, such as nitinol. In these embodiments, the drug-delivery features 1350 can remain engaged with or penetrating a portion of the body lumen after the expanded frame 1330 and struts 1313 bio-resorb. After the expanded frame 1330 and struts 1313 bio-resorb, the body lumen where the stent 1300 had been expanded is no longer partially occluded by the frame 1330 and the struts 1313 allowing for larger volumes of fluids, such as aqueous pharmaceutical compositions, to pass through the body lumen and contact the luminal wall. The drug-delivery features 1350 may also be formed of a bio-resorbable material and, once the stent 1300 has bio-resorbed, the spaces in the body lumen wall vacated by the drug-delivery features 1350 can be contacted by the fluids passing through the body lumen. In this way, the stent 1300 can increase a surface area of the body lumen wall contacted by the fluid.

As illustrated in FIG. 13, the stent 1300 includes drug-delivery features 1350 carried by the struts 1310. The drug-delivery features 1350 may also be carried by more than one strut 1310, the frame 1330, or a combination thereof. The drug-delivery features 1350 may be integrally formed with the struts 1310, for example by bending or twisting a portion of one or more struts and/or the frame 1330 away from a longitudinal axis of the stent 1300 or, alternatively, the drug-delivery features 1350 may be separate, discrete components that are attached to desired locations along the struts 1310 and/or the frame 1330.

FIGS. 14A and 14B are isometric views of portions of drug-eluting expandable structures (e.g., stents) having drug-delivery features configured in accordance with further embodiments of the present technology. In the embodiment illustrated in FIG. 14A, for example, the drug-delivery features 1460 have a radially elongated, curved, needle-like arrangement. A portion of a stent 1400 including a frame 1430 and a plurality of struts 1410 having protruding features 1460 (e.g., spikes, sharpened/tapered members, barbs, needles) configured to engage with and/or penetrate a portion of the body lumen, such as a vessel. The protruding features 1460 are integrally formed portions of the struts 1410 and extend radially outward away from the stent 1400 toward the target portion of the body lumen. In some embodiments, the drug-delivery features 1460 can provide for penetration through a body lumen wall (e.g., a vessel wall) to deliver drugs directly into target tissue beyond the vessel wall. In other embodiments, the drug-delivery features 1460 can be configured to detach from the frame 1430 and remain at least partially penetrated within the vessel wall. In these embodiments, detached drug delivery features 1460 can be configured for short-term or long-term delivery of the drug to the target tissue within the vessel wall. Vessels and target tissues are described elsewhere herein.

In the embodiment illustrated in FIG. 14B, for example, a stent 1470 includes a strut 1410 having drug-delivery features 1482 having one or more reservoirs 1480, and a drug carried by the reservoir. The reservoir 1480 can at least partially contain the drug and protect it from being prematurely released (e.g., via scraping during delivery of the associated stent through a catheter). In various embodiments, the reservoir 1480 and/or the drug-delivery feature 1482 can either be configured to de-couple from the strut 1410 and remain in the vessel wall, or engage with the wall to deliver the drug and remain fixedly coupled to the strut 1410. Further, the drug-delivery features 1482 may have a variety of different shapes, sizes, and configurations. The drug-delivery features disclosed herein enhances engagement with and/or penetration of the lumen wall, provides enhanced drug-delivery, and allows for better treatment at the desired location. In some embodiments, such as non drug-eluting stents, the drug-delivery features 1482 can be protruding features.

The material(s) for forming the frame, struts, and/or drug-delivery features described herein can be selected based on mechanical and/or thermal properties, such as strength, ductility, hardness, elasticity, flexibility, flexural modulus, flexural strength, plasticity, stiffness, emissivity, thermal conductivity, specific heat, thermal diffusivity, thermal expansion, any of a variety of other properties, or a combination thereof. If formed from a material having thermal properties, the material can be activated to deliver thermal treatment to the desired treatment site. Regardless of the material, the frame, struts, and/or drug-delivery features can be formed from a tube or a wire, such as a solid wire, by laser cutting or other suitable techniques. When formed from the wire, a portion of the wire can be removed by chemical etching or another suitable method to create an inner dimension of the stent.

In accordance with the present technology, stents (e.g., the frame and the struts) can be sized and shaped for placement within various body lumens, including blood vessels, while not rupturing the vessel. For example, several stents and other structures configured in accordance with the present technology can have radial strength that allows for features of the body lumen (e.g., vessel wall) to receive drugs without dissection or damage thereto. Vessels in which the stents described herein may be sized and shaped for placement include arteries, such as coronary arteries, peripheral arteries, carotid arteries, circle of willis, anterior cerebral artery, middle cerebral artery, posterior cerebral artery, any of the lenticulostriate arteries, renal arteries, femoral arteries, veins, such as cerebral veins, saphenous veins, arteriovenous fistulas, or any other vessel that may contain a treatment site. Stents can have a variety of shapes, including a cube, a rectangular prism, a cylinder, a cone, a pyramid, or variations thereof.

Stents and other structures having drug-delivery features configured in accordance with the present technology can include a variety of dimensions (in both the low-profile delivery state and expanded deployed state). These embodiments can provide for expansion that enables usage in a variety of situations covering a wide range of dimensions, such as to treat and/or prevent dissection. Regardless of the shape, stents can have a length of about 0.25 mm, about 0.5 mm, about 1 mm, about 2 mm, about 3 mm, about 4 mm, about 5 mm, about 6 mm, about 7 mm, about 8 mm, about 9 mm, about 10 mm, about 12 mm, about 14 mm, about 16 mm, about 18 mm, about 20 mm, about 30 mm, about 40 mm, about 50 mm, about 60 mm, about 70 mm, about 80 mm, about 90 mm, or about 100 mm. In addition, a stent shaped into a cube, a rectangular prism, or a pyramid can have a width of about 0.25 mm, about 0.5 mm, about 1 mm, about 2 mm, about 3 mm, about 4 mm, about 5 mm, about 6 mm, about 7 mm, about 8 mm, about 9 mm, about 10 mm, about 12 mm, about 14 mm, about 16 mm, about 18 mm, about 20 mm, about 25 mm, or about 30 mm. Moreover, a stent shaped into a cylinder or a cone can have a diameter of about 0.25 mm, about 0.5 mm, about 1 mm, about 2 mm, about 3 mm, about 4 mm, about 5 mm, about 6 mm, about 7 mm, about 8 mm, about 9 mm, about 10 mm, about 12 mm, about 14 mm, about 16 mm, about 18 mm, about 20 mm, about 25 mm, about 30 mm, about 35 mm, about 40 mm, or about 50 mm. The width or the diameter of the stent can decrementally decrease along a length of the stent. In addition, the stent can be sized and shaped to prepare the body lumen for certain procedures, such as a stent placement procedure.

The stent 1300, other stents, and other expandable structures in the expanded state and configured in accordance with the present technology can have a cross-sectional dimension of about 2 mm to about 10 mm, inclusive of the expanded drug-delivery features. For example, a frame configured in accordance with the present technology (such as frame 1330) can have a cross-sectional dimension of about 1 mm to about 9 mm and the drug-delivery features can each have a length from about 0.1 mm to about 1.5 mm. In some embodiments, the stent has an overall cross-sectional dimension of about 4 mm with the frame 1330 having a cross-sectional dimension of about 2 mm and the drug-delivery features each having a length of about 1 mm. In some embodiments, the stent has an overall cross-sectional dimension of about 6 mm with the frame 1330 having a cross-sectional dimension of about 4 mm and the drug-delivery features each having a length of about 1 mm. In further embodiments, the drug-delivery features can have a plurality of lengths such that the length of the drug-delivery features of a stent or other expandable structure differs. For example, a stent can include drug-delivery features having a length of about 0.2 mm, about 0.5 mm, and about 1 mm.

Profiles of the stents or other structures can be sized such that the stents or other structures are compatible with a wide range of catheter sizes. Embodiments in accordance with the present technology can include stents or other structures designed to receive a guidewire, such as guidewires having a diameter of 0.010, 0.014, 0.018, 0.035, or 0.038 inch. In several embodiments, the stent or scaffold structure can be sized and designed for delivery via a micro-catheter that it is pushed through. In some embodiments, stents or structures configured in accordance with the present technology can be incorporated into a delivery system, including modular or single unit delivery systems.

Stents and other structures described herein can include a marking for visualization of the stent within the body lumen, such as one or more radiopaque markers (see radiopaque markers 810 of FIGS. 8A, 8B and 9). The radiopaque markers can be formed from Clearfil Photo Core PLT®, tantalum, titanium, tungsten, barium sulfate, and zirconium oxide, or another suitable radiopaque marking. The markings can be formed on a proximal portion of the stent, a distal portion, an intermediate portion, or a combination thereof. The markings can be a band, a coil, a clip, filled into one or more portions of a tube in the stent, plated onto one or more portions of the stent, or a combination thereof. Regardless of the type of marking, the marking can be coined, swaged, wrapped, or encased along, or onto any portion of the stent.

Stents and other structures configured in accordance with the present technology can be flexible enough to track through various anatomical features, including those having a curvature. The flexible properties of the stent and other structures can be provided by the material from they are formed. In addition, flexible properties can also be provided by fracturing one or more of the members engaging with and extending between two or more rows of struts. Additionally, the stent or other structure can be readily deployed and expanded, and retracted and contracted. The stent or other structure can also be readily repositioned within a vessel or other body lumen.

In several embodiments, a drug-eluting compound is coated onto at least a portion of the drug-delivery features, the frame, the struts, and/or the balloon. The coating can be any suitable coating known to one of ordinary skill in the art suitable to deliver the drug to the wall. For example, suitable coatings include, but are not limited to a snow coating or a crystalline coating having edges configured to remain in the wall. The drug-eluting compound can be a synthetic or biological polymer coated into a variety of different patterns and thicknesses suitable for delivering the drug contained therein. In other embodiments, the drug-delivery features themselves may be composed of drug-eluting materials. The drug carried by the drug-eluting compound and/or the drug-delivery features in accordance with the present technology can be any drug suitable for treating the treatment site in which the stent will be placed and may or may not include an excipient. For example, the drug can be an anti-proliferative, an anti-neoplastic, a migration inhibitor, an enhanced healing factor, an immunosuppressive, an anti-thrombotic, a blood thinner, or a radioactive compound. Examples of anti-neoplastics include, but are not limited to, siroliums, tacrolimus, everolimus, leflunomide, M-prednisolone, dexamethasone, cyclosporine, mycophenolic acid, mizoribine, interferon, and tranilast. Examples of anti-proliferatives include, but are not limited to, taxol/paclitaxel, actinomycin, methotrexate, angiopeptin, vincristine, mitmycine, statins, c-myc antisense, Abbot ABT-578, RestinASE, 2-chloro-deoxyadenosine, and PCNA ribozyme. Examples of migration inhibitors, but are not limited to, include batimistat, prolyl hydrosylase, halofunginone, c-preteinase inhibitors, and probucol. Examples of enhanced healing factors include, but are not limited to, BCP 671, VEGF, estradiols, NO donor compounds, and EPC antibodies. Examples, of radioactive compounds include, but are not limited to, strontium-89 chloride (Metastron®), samarium-153 (Quadramet®), radium-223 dichloride (Xofigo®), yttrium-90, and iodine-131. In some embodiments, the drug-eluting compound and/or the drug-delivery features can carry more than one drug.

In some embodiments, the drug-delivery features can include textured (e.g., ribbed) surfaces which is expected to provide greater surface area for drug-delivery. Moreover, any drug-delivery features can include a textured surface such as a ribbed surface (vertical, horizontal, radial, or circular relative to a longitudinal plane of the drug-delivery feature), a cross-hatched surface, an isotropic surface, or other surface types suitable for providing greater surface area for drug-delivery.

The drug-delivery features can be sized and shaped to engage with and/or penetrate an occlusion, a neointima, an intima, an internal elastic lamina (IEL) a media, an external elastic lamina (EEL), an adventitia, or a combination thereof. The drug-delivery features can also be sized and shaped to engage with and/or penetrate a tissue and/or structure adjacent to the body lumen in which the stent is to be placed while not rupturing the body lumen. For example, the stent can include square drug-delivery features sized and configured to penetrate into the intima and/or the media of a body lumen, pointed drug-delivery features sized and configured to penetrate and extend into the media, and/or the IEL. In addition, drug-delivery features can be configured to bend in one or more directions relative to a longitudinal axis of the stent to engage with and/or penetrate a portion of the body lumen described herein. In several embodiments, the drug-delivery features can penetrate deeper into the wall of a diseased body lumen, such as a vessel, compared to a stent lacking drug-delivery features. In addition, the stent can allow for blood to flow even while in the expanded position and with drug-eluting on-going.

Various drug-delivery features described herein can deliver drugs deeper into a vessel wall than possible via angioplasty balloons or other existing devices. In addition to carrying one or more drugs for treatment of the site, the drug-delivery features can also carry a molecule suitable for degrading a portion of the occlusion, neointima, and/or intima to allow the drug-delivery features to penetrate deeper in to the vessel wall than without the molecule. For example, the molecule suitable for degradation can be an enzyme, such as elastase, collagenase, or a proteinase, such as, metalloproteinases, serine proteinases, cysteine proteinases, extracellular sulfatases, hyaluronidases, lysyl oxidases, lysyl hydroxylases, or a combination thereof.

Further, it will also be appreciated that stents configured in accordance with the present technology can carry one or more drug-delivery features on one or more portions of the stent. For example, the stents can carry about 5 drug-delivery features, about 10 drug-delivery features, about 15 drug-delivery features, about 20 drug-delivery features, about 30 drug-delivery features, about 40 drug-delivery features, about 50 drug-delivery features, about 60 drug-delivery features, about 70 drug-delivery features, about 80 drug-delivery features, about 90 drug-delivery features, or about 100 drug-delivery features. The drug-delivery features can be carried by the frame, the struts, or a combination thereof. The number of drug-delivery features can vary depending upon, for example, the target treatment site, the type of drug being delivered, and size of the stent, etc. In addition, the drug-delivery features carried by the stent can be different types of the drug-delivery features disclosed herein.

In some embodiments, once positioned against a body lumen wall (e.g., a vessel wall), tissue and/or fluid can interact with the drug-delivery feature to dissolve the drug and selectively release it from the reservoir. In other embodiments, the drug-delivery feature can be configured to deliver the drug via a variety of means once the stent is expanded. Drug-delivery features are accordingly expected to provide an effective means for selectively delivering a drug to a desired location, while reducing inadvertent loss or release of drugs. In other embodiments, the stent can include more than one drug-delivery feature, or a drug-delivery feature having more than one reservoir. In several embodiments, the stent including drug-delivery features configured in accordance with the present technology can have the drug-delivery feature, such as the coating or the reservoir, concealed (e.g., recessed) until the stent is positioned at the treatment site. Once positioned at the target site, the drug-delivery feature can be revealed (e.g., expanded/projected, etc.) during and/or after expansion of the stent. This is expected to reduce any loss of the drug carried by the drug-delivery feature during delivery to the treatment site.

Although the illustrated embodiments of FIGS. 13 and 14A-14B do not include protruding features, such as, drug-delivery features having a variety of shapes, it is to be understood that other embodiments can include drug-delivery features. For example, the drug-delivery features can include protruding features sized and shaped for placement within various body lumens, including vessels as described herein. The sizes and shapes can be selected to achieve a desired engagement with or penetration of certain features (e.g., target tissues) of the body lumen in which the stent will be placed. The protruding features can have a number of shapes, including but not limited to, a cube, a square, a rectangular prism, a cylinder, a circle, a cone, a pyramid, curved-spikes, or other pointed shape. Any of these shapes can have flat, dull, pointed, and/or sharp distal portions.

In some embodiments, the stents can further include a material (e.g., PTFE, Dacron, polyamides, such as nylon and/or polyurethane based materials, silicone, etc.) positioned over a stent, scaffold or other structure having drug-delivery features covering at least a portion of the outer surface area. In some embodiments, the material covers the entire outer surface area. The material can be a mesh or a braid. In some embodiments, the material can be configured to increase a surface area of the stent useful for providing additional surface area of the stent for coating with a drug. In other embodiments, the material can further be configured to allow blood flow through the inner diameter of the stent and/or limit blood flow to an outer dimension of the stent. In additional embodiments, the material can create a barrier between fluid flow (e.g., blood flow) and the drug-delivery locations. In addition, the material can be configured to prevent debris from the wall of the body lumen from entering the bloodstream. In such embodiments, the associated systems and devices can be used for temporary dissection tacking or coverage of a region that may have been perforated during a procedure.

Figure 15:
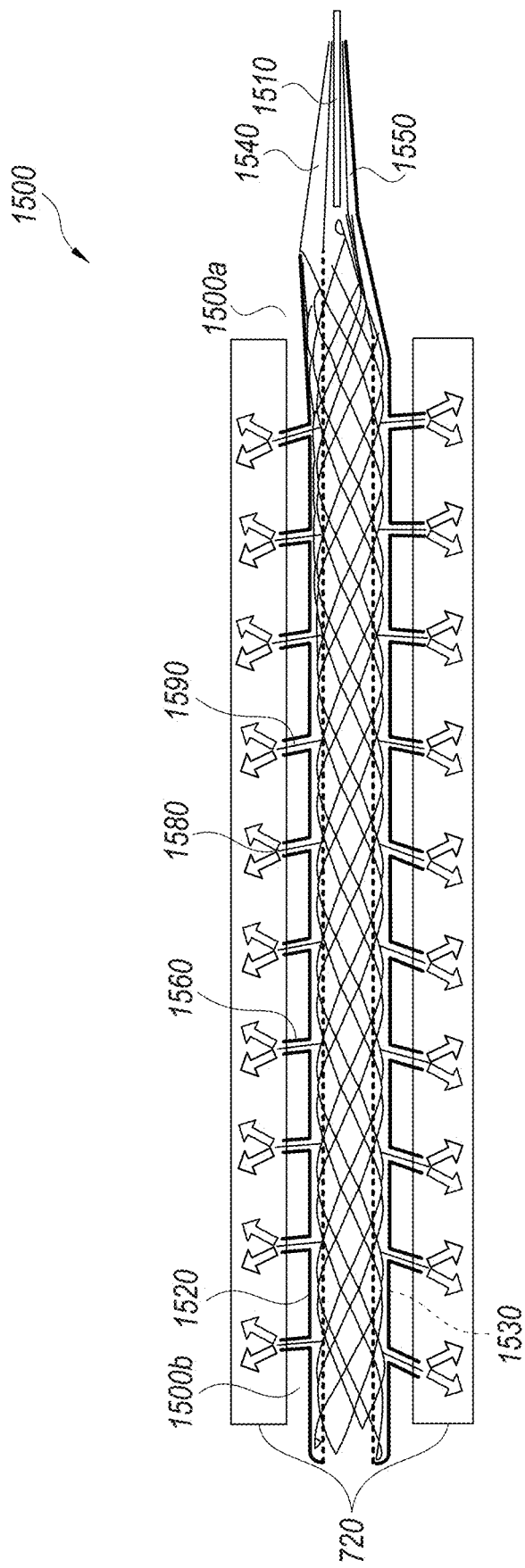
FIG. 15 is a partially schematic side view of a drug-eluting expandable structure having drug-delivery features in the deployed state within a body lumen and configured in accordance with an embodiment of the present technology.

FIG. 15 is a partially schematic side view of a stent 1500 having a chamber 1540 and drug-delivery features 1590 in the expanded state within a body lumen 510 and configured in accordance with an embodiment of the present technology. In the illustrated embodiment, the stent 1500 is sheathed by an outer layer 1520 (e.g., a cover) and an inner layer 1530 (e.g., a liner). Each of the outer and inner layers 1520 and 1530, respectively, can be formed from materials including a polymer, high-density polyethylene (HDPE), polytetrafluoroethylene, silicone, Pebex® (polyether block amide) or a combination thereof. In some embodiments, each of the layers are formed from the same materials. In other embodiments, each of the layers are formed from different materials.

In the illustrated embodiment, the outer layer 1520 is continuous with the inner layer 1530 and defines, at least in part, chamber 1540 that is configured to carry one or more drugs for delivery into the vessel wall. In other embodiments, stent 1500 can include additional chambers formed from the outer and inner layers, 1520 and 1530, or stent 1500 can include additional layers configured to form one or more chambers. As illustrated, chamber 1540 includes an inlet port 1550 at a proximal zone 1500a of the stent 1500. In other embodiments, the stent 1500 can include additional ports, such as inlet and/or outlet ports disposed at other zones of the stent 1500 (e.g., a distal zone 1500b, and/or a proximal zone 1500a).

The chamber 1540 further includes conduits 1560 fluidly coupled to the chamber and sheathing a plurality of the drug-delivery features 1590. As illustrated, each of the conduits 1560 include an outlet port 1580 at a terminal end. In other embodiments, the outlet port 1580 can be located elsewhere on the conduit 1560. In further embodiments, the chamber 1540 and conduits 1560 can be fluidly connected to connector 150 of system 100. The connector 150 can be configured to infuse fluid containing the drug through port 152 (e.g., flush port) into chamber 1540 and to release the fluid from the chamber 1540.

The conduits 1560 are configured to release the drug from the chamber 1540 through the outlet port 1580 and into the wall after the drug-delivery features 1590 have pierced into the lumen wall. One or more of the conduits 1560 can at least partially contain the drug and protect it from being prematurely released (e.g., via scraping during delivery of the associated stent through a catheter) into the lumen wall. Once positioned against, or pierced into, a body lumen wall (e.g., a vessel wall), tissue and/or fluid can interact with the drug-delivery feature 1590, one or more conduits 1560, and/or one or more openings 1580 to selectively release the drug from the chamber 1540. In other embodiments, the drug-delivery feature 1590 can be configured to deliver the drug via a variety of means once the stent 1500 is expanded. Drug-delivery feature 1590 is accordingly expected to provide an effective means for selectively delivering a drug to a desired location, while reducing inadvertent loss or release of drugs.

In several embodiments, the stent 1500 including drug-delivery features 1590 configured in accordance with the present technology can have the drug-delivery feature 1590, the chamber 1540, the conduit 1560, and/or the conduit opening 1580 concealed (e.g., recessed) until the stent 1500 is positioned at the desired location (e.g., target site or treatment site). Once positioned at the treatment site, the drug-delivery feature 1590, the chamber 1540, the conduit 1560, and/or the conduit opening 1580 can be revealed (e.g., expanded/projected, etc.) during and/or after expansion of the stent 1500. This is expected to reduce any loss of the drug carried by the drug-delivery feature 1590 during delivery to the treatment site.

Figure 16:
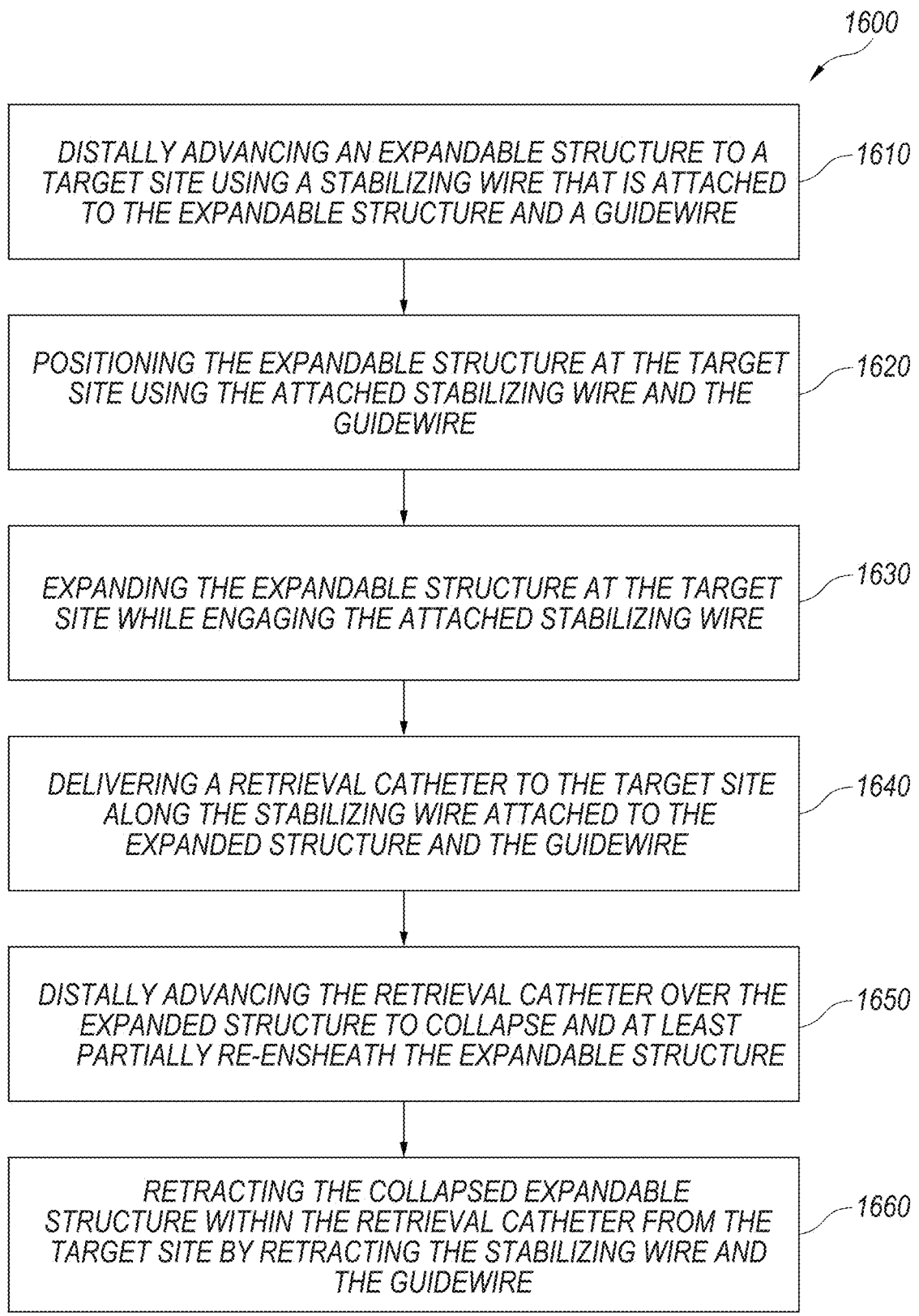
FIG. 16 is a block diagram illustrating a method of delivering and retrieving an expandable structure in accordance with embodiments of the present technology.

III. Methods of Delivering and Retrieving Stents and Other Structures and Associated Systems and Methods FIG. 16 is a block diagram illustrating a method ("method 1600") of delivering and retrieving an expandable structure in accordance with embodiments of the present technology. The expandable structure is a stent, such as a stent having one or more drug-delivery features. At block 1610, the method 1600 can include distally advancing the expandable structure to a target site in a patient using a stabilizing wire attached to the expandable structure. As described in greater detail above, the stabilizing wire can have a suitable length for maintaining a position of the expandable structure at the target site while the outer shaft and/or the guidewire is distally advanced and/or proximally retracted. In some embodiments, for example, the position of the stabilizing wire is maintained by actuating a portion of the stabilizing wire positioned extracorporeally. In some embodiments, the method 1600 further includes delivering a guidewire, such as a 0.014 inch guidewire, to the target site. For example, the guidewire can be inserted into the inner shaft, such as a delivery catheter, which can then be inserted into the outer shaft, such as a guide catheter, introducer sheath, or the like.

At block 1620, the method 1600 includes intravascularly positioning the expandable structure at the target site using the attached stabilizing wire and the guidewire. Positioning the stent further includes advancing the outer shaft to the treatment site which, optionally, may have previously been subject to another procedure (e.g., a percutaneous angioplasty). In some embodiments, the stent is positioned using fluoroscopic guidance and may include markers that can be aligned at the target site by a clinician.

At block 1630, the method 1600 includes transforming the expandable structure between a low-profile delivery state and an expanded, deployed state at the target site while engaging the attached stabilizing wire. For example, the outer shaft can be proximally retracted until one or more radiopaque markers at a distal end of the stent are detected using suitable visualization techniques. After the distal end is visualized, the stabilizing wire can be fixed into position using a fixation mechanism coupled to the stabilizing wire. In some embodiments, the fixation mechanism can be adjusted to maintain the fixed position of the stabilizing wire and the stent attached thereto while the outer shaft (and optionally the inner shaft) are proximally retracted (and optionally, distally advanced) and removed from the body lumen.

After the stent has been delivered to the target site and expanded, a balloon can be delivered into at least a portion of the expanded stent lumen by inserting the balloon over the guidewire using any number of standard techniques until a distal portion of the balloon is aligned with a distal portion of the stent. For example, the balloon may include a distal radiopaque marker that can be visualized using fluoroscopic guidance. In some embodiments, the balloon can be a percutaneous transluminal angioplasty balloon (e.g., about 4 mm by about 60 mm, over a 0.014 inch guidewire). As discussed with respect to block 1630, the stabilizing wire can be fixed into position to maintain the position of the expanded stent while the balloon is delivered, expanded (e.g., inflated), collapsed (e.g., deflated), and withdrawn.

At block 1640, the method 1600 includes delivering a retrieval catheter to the target site along the stabilizing wire that is attached to the expanded structure and the guidewire. For example, the retrieval catheter can be delivered such that a channel fluidly coupled to an opening in a distal portion, such as an opening in a tip, carries the stabilizing wire and the guidewire as the retrieval catheter is delivered to the body lumen. In some embodiments, the retrieval catheter can be delivered to the target site using fluoroscopy to visualize a location of the distal portion of the retrieval catheter.

At block 1650, the method 1600 also includes distally advancing the retrieval catheter over the expanded structure to collapse and at least partially resheath the expandable structure. In some embodiments, a distal end of the retrieval catheter tip can engage with a proximal portion of the expanded stent at the target site and at least partially collapse the stent. The retrieval catheter, for example, can be distally advanced until the collapsed stent is resheathed within the distal portion of the retrieval catheter. For example, one or more radiopaque markers disposed on the proximal and distal portions of the stent can be visualized to determine when the stent is resheathed within the distal portion of the retrieval catheter, such as visualized proximal to the one or more radiopaque markers coupled to a distal portion of the retrieval catheter.

At block 1660, the method 1600 further includes advancing the collapsed expandable structure within the retrieval catheter from the target site by retracting the stabilizing wire and the guidewire. After block 1660, the method 1600 can also include withdrawing the retrieval catheter from the body lumen to remove the collapsed stent ensheathed therein. Optionally, the method 1600 can continue by using any number of intraluminal techniques, such as delivering a second stent and/or second balloon to the target site.

IV. Additional Embodiments of Stents and Other Structures and Associated Systems and Methods The embodiments described herein provide delivery systems for one or more structures having a means for delivering drugs to a specific region within a body lumen, such as the vasculature, while still allowing fluid (e.g., blood) to flow through the treatment area where the structure has been placed and/or other devices or treatment means within the adjacent body lumen. In some embodiments, the fluid is temporary prevented from flowing through the treatment area while one or more regions of systems configured in accordance with the present technology (e.g., system 100) is delivered, deployed, positioned, and/or removed from the body lumen. In addition, the delivery systems can be configured to prepare the body lumen for treatment, by raking the stent, pulling the stent, turning the stent, or a combination thereof, proximal or distal to the treatment site. In other embodiments, the delivery systems can be configured to rotate the stent when mechanical force is applied.

The systems disclosed herein can provide for adjustment, recapture, and/or redeployment of the associated stents or other structures, and/or deployment of a different stent or other structure, allowing a practitioner to more effectively to treat a desired region more accurately and deliberately. In several embodiments, the stent or other delivery structure can be deployed for a temporary period (e.g., for less than 24 hours), and then retracted and removed. In these embodiments, the drug-delivery features can engage with and/or pierce the lumen wall and remain therein after the stent or other delivery structure is removed, or can be retracted and removed with the stent or other delivery structure. The stent can be configured to self-expand, or partially self-expand, when deployed from the delivery system and also be configured to further expand within the body lumen when the balloon is expanded therein. The stent can also be configured to post-dilate when removed from the body lumen. In other embodiments, the stent or other delivery structure can be deployed for a long-term temporary period (e.g., for less than 2 weeks, less than one month, less than 6 months, less than one year), and then retracted and removed. In some embodiments, a different stent or delivery structure can be deployed after a first stent or delivery structure has been retraced and removed. The duration of deployment and duration after removal before deployment of the different stent or delivery structure can vary from minutes, to hours, to days, to weeks, to months, or to years. In these embodiments, removal of the first stent or delivery structure and deployment of a different stent or delivery structure can occur once, twice, three times, four times, five times, six times, seven times, eight times, nine times, or ten times. Moreover, the embodiments described herein can allow for a lower profile system than currently available balloons.

In the embodiments described herein and other embodiments configured in accordance with the present technology, stents and other expandable structures may include non-drug-delivery features, such as deployable and/or expandable features, that are not configured for delivering a drug to a target location. For example, stents and other expandable structures configured in accordance with the present technology can include one or more drug-delivery features, one or more non-drug-delivery features, or combinations thereof.

While many embodiments of the stents and/or structures described herein include stents, additional embodiments of the expandable elements, such as stents and/or structures, can include non drug-eluting stents and/or non drug-eluting structures. In these embodiments, the non drug-eluting stents may include one or more protruding members, such as spikes. The spikes can be configured to engage with and/or penetrate a portion of the body lumen or vessel. For example, the spikes can penetrate the vessel wall, thereby reducing and/or eliminating an elasticity of the vessel wall. In these embodiments, the protruding members can be configured to prevent the vessel wall from progressing inward toward the body lumen and restricting and/or constricting flow therein. The protruding members can be integrally formed with the struts, or disposed on the surface of the struts, extending radially outward from the struts toward the target tissue.

V. Additional Examples

The following examples are illustrative of several embodiments of the present technology.

1. A stent system, the system comprising:
a connector having a connector lumen;
an elongated outer shaft fixedly coupled to a distal end of the connector and to an outer shaft hub, the outer shaft having an outer shaft lumen;
an elongated pusher shaft slideably disposed within the outer shaft lumen and the connector lumen and fixedly coupled to a pusher shaft hub, the pusher shaft having first pusher shaft lumen and a second pusher shaft lumen;
an elongated inner shaft slideably disposed within the first pusher shaft lumen having an inner lumen; and
a stent shaft slideably disposed within the second pusher shaft lumen, the stent shaft fixedly coupled to a proximal end of a stent carried by the system for delivery to a target location within a human patient.

2. The system of example 1, further comprising a balloon slideably disposed within the inner shaft lumen.

3. The system of examples 1 and 2, further comprising a force element fixedly coupled to the outer shaft.

4. The system of examples 1-3 wherein the element is disposed on the outer shaft distally from the outer shaft hub.

5. The system of examples 1-4 wherein the connector further comprises a port coupled to the connector lumen.

6. The system of examples 1-5 wherein the outer shaft hub is disposed on the outer shaft distally from the connector.

7. The system of examples 1-6 wherein the pusher shaft hub is disposed on the outer shaft proximally from the connector.

8. The system of examples 1-7, further comprising a stent shaft hub fixedly or slideably coupled to the stent shaft.

9. The system of examples 1-8 wherein the stent shaft hub is disposed on the stent shaft proximally from the connector.

10. The system of examples 1-9 wherein the pusher shaft hub is disposed on the pusher shaft distally from the stent shaft hub.

11. The system of examples 1-10 wherein the pusher shaft hub further comprises a first mating feature and the stent shaft hub further comprises a second mating feature, the first mating feature sized and shaped to engage with the second mating feature.

12. The system of examples 1-11 wherein the first mating feature is engaged with the second mating feature.

13. The system of examples 1-12 wherein the inner shaft lumen is partially sheathed by the inner shaft.

14. The system of examples 1-13 wherein the second pusher shaft lumen is partially sheathed by a portion of the pusher shaft.

15. The system of examples 1-14, further comprising a guidewire slideably disposed within the inner shaft lumen.

16. The system of examples 1-15 wherein the inner shaft is a guidewire tube.

17. The system of examples 1-16 wherein the element is a strain relief shrink tube.

18. The system of examples 1-17 wherein the stent comprises:
a radially expandable cylindrical frame or braided mesh having a plurality of struts or wires; and
a plurality of protruding features carried by one or more struts.

19. The system of examples 1-18 wherein the plurality of protruding features comprise a first set of protruding features carried by a first strut and a second set of protruding features carried by a second, different strut.

20. The system of examples 1-19 wherein the plurality protruding features are separate, discrete components attached to the strut.

21. The system of examples 1-20 wherein the plurality of protruding features comprise reservoirs integrally formed therein.

22. The system of examples 1-21 wherein the plurality of protruding features, the stent, or a combination thereof are coated with a substrate.

23. The system of examples 1-22 wherein the stent further comprises a radiopaque marker.

24. The system of examples 1-23 wherein the stent, a portion of the stent, the plurality of protruding features, a portion of the plurality of features, a portion of each of the plurality of features, or a combination thereof are biodegradable.

25. A system for delivering, deploying, and recapturing a stent within a body lumen of a patient, the system comprising:
   an elongated outer shaft configured to sheath at least a zone of the stent;
   an outer shaft hub configured to proximally retract and/or distally advance the outer shaft, an elongated pusher shaft configured to distally advance the stent; and
   a pusher shaft hub configured to proximally retract and/or distally advance the pusher shaft,
   wherein the stent is configured to transform between a low-profile delivery state and an expanded deployed state, and
   wherein, in the deployed state, a plurality of protruding features carried by one or more struts extend radially outwardly away from the strut and are configured to engage a first portion of the body lumen.

26. The system of example 25, further comprising an elongated inner shaft configured to position a guidewire within the body lumen, the inner shaft having a partially enclosed inner shaft lumen partially configured to release the guidewire.

27. The system of examples 25 and 26 wherein the guidewire is configured to be released to remove a first catheter from the system and insert a second catheter into the system.

28. The system of examples 25-27 wherein the stent is self-expanding.

29. The system of examples 25-28 wherein the stent is configured to be mechanically actuated to transform the stent between the delivery state and the deployed state.

30. The system of examples 25-29, further comprising a balloon configured to expand when positioned within a lumen of the stent.

31. The system of examples 25-30 wherein when the balloon is expanded, the stent transforms from the delivery state to the deployed state.

32. The system of examples 25-31, further comprising a strain relief element configured to prevent a first of the outer shaft from collapsing upon a second portion of the outer shaft.

33. The system of examples 25-32 wherein the pusher shaft is configured to prevent the stent from advancing proximally while the stent is transitioned from the delivery state to the deployed state.

34. The system of examples 25-33, further comprising a stent shaft and a stent shaft hub, the stent shaft hub fixedly coupled to the stent shaft and configured to maintain a position of the stent.

35. The system of examples 25-34 wherein the stent is further configured to transform from the deployed state to a low-profile removal state, and in the removal state, the plurality of protruding features retract inwardly toward the struts, and the outer shaft is configured to resheath the stent.

36. The system of examples 25-35 wherein, when the stent is transitioned from the deployment state to a removal state, the stent shaft hub maintains a position of the stent during the transition.

37. A method for delivering and deploying a stent within a body lumen of a human patient, the method comprising:
   intravascularly delivering an elongated shaft ensheathing the stent to a target treatment site within the body lumen of the patient, wherein the stent comprises
      a radially expandable cylindrical frame having a plurality of struts; and
      a plurality of protruding features carried by one or more struts and configured to deliver a drug to a treatment site within the body lumen of the patient;
   proximally retracting the elongated shaft to at least partially unsheath the stent;
   distally advancing a balloon in a low-profile delivery state into a lumen of the stent;
   radially expanding the stent to an expanded state by transforming the balloon from the low-profile delivery state to an expanded state; and
   piercing through a portion of a wall of the patient's lumen with one or more protruding features.

38. The method of example 37, further comprising positioning the stent at the target treatment site by distally advancing a pusher shaft coupled to a proximal end of the stent through a lumen of the elongated shaft.

39. The method of examples 37 and 38, further comprising removing the pusher shaft from the lumen of the elongated shaft.

40. The method of examples 37-39, further comprising radially collapsing the stent from the expanded state to the low-profile state.

41. The method of examples 37-40, further comprising positioning the pusher shaft within the lumen of the elongated shaft, engaging a distal terminus of the pusher shaft with a proximal end of the stent, and removing the stent from the lumen.

42. The method of examples 37-41, further comprising distally advancing the elongated shaft to sheath the collapsed stent and proximally retracting the elongated shaft.

43. The method of examples 37-42 wherein one or more of the plurality of protruding features detach from the frame after piercing the portion of a wall of the patient's body lumen.

44. The method of examples 37-43 wherein the plurality of protruding features comprise reservoirs integrally formed therein and/or wherein the plurality of protruding features, the stent, or a combination thereof are coated with a substrate configured to deliver a drug carried therein to the patient, to prevent clotting, to prevent occlusion of the stent, or a combination thereof.

45. The method of examples 37-44 wherein the frame comprises a chamber coupled to the stent and extending along a length thereof.

46. The method of examples 37-45 wherein one or more of the plurality of protruding features have a conduit fluidly coupled to the reservoirs, the chamber, or a combination thereof.

47. The method of examples 37-46, when the frame is in the expanded state within the body lumen, the stent is configured to allow one or more substances to flow from the reservoirs, the chamber, or a combination thereof, through at least one of the drug-delivery feature conduits, and the wall.

48. A delivery system for a expandable element, the delivery system comprising:
   a connector having a connector lumen;
   an outer shaft hub;
   an elongated outer shaft fixedly coupled to a distal end of the connector and the outer shaft hub, wherein the elongated outer shaft includes an outer shaft lumen;
   a expandable element carried by a distal portion of the elongated outer shaft and configured for delivery to a target location within a human patient;
   an elongated positioning shaft slideably disposed within the outer shaft lumen and extending through an opening in the connector, wherein a distal portion of the elongated positioning shaft is fixedly coupled to the expandable element; and an elongated inner shaft slideably disposed within the outer shaft lumen.

49. The delivery system of example 48 wherein the inner shaft comprises a guidewire lumen.

50. The delivery system of example 49, further comprising a guidewire slideably disposed within the guidewire lumen.

51. The delivery system of examples 48-50 wherein the expandable element comprises:

a radially expandable cylindrical frame or braided mesh having a plurality of struts or wires; and a plurality of protruding features carried by one or more struts.

52. The delivery system of example 51 wherein the plurality of protruding features comprise a first set of protruding features carried by a first strut and a second set of protruding features carried by a second, different strut.

53. The delivery system of example 51 wherein the plurality of protruding features are separate, discrete components attached to the strut.

54. The delivery system of example 51 wherein the plurality of protruding features comprise reservoirs integrally formed therein.

55. The delivery system of example 51 wherein the plurality of protruding features, the stent, or a combination thereof are at least partially covered with a material.

56. The delivery system of examples 48-55 wherein the expandable element further comprises a radiopaque marker.

57. The delivery system of example 56 wherein the radiopaque marker is disposed on a proximal portion of the elongated positioning shaft, a distal portion of the elongated positioning shaft, or a combination thereof.

58. The delivery system of examples 48-57 wherein the positioning shaft is a stabilizing shaft.

59. The delivery system of examples 48-58 wherein the expandable element, a portion of the expandable element, the plurality of protruding features, a portion of the plurality of features, a portion of each of the plurality of features, or a combination thereof are biodegradable.

60. The delivery system of examples 48-59 wherein the elongated positioning shaft is configured to maintain a position of the expandable element at the target location within the patient during therapy.

61. The delivery system of examples 48-60 wherein the elongated positioning shaft is configured to maintain a position of the expandable element while the elongated outer shaft, the elongated inner shaft, a different shaft, or a combination thereof is intravascularly positioned within the human patient.

A reference to an element in the singular is not intended to mean one and only one unless specifically so stated, but rather one or more. For example, "a" module may refer to one or more modules. An element proceeded by "a," "an," "the," or "said" does not, without further constraints, preclude the existence of additional same elements.

Headings and subheadings, if any, are used for convenience only and do not limit the invention. The word exemplary is used to mean serving as an example or illustration. To the extent that the term include, have, or the like is used, such term is intended to be inclusive in a manner similar to the term comprise as comprise is interpreted when employed as a transitional word in a claim. Relational terms such as first and second and the like may be used to distinguish one entity or action from another without necessarily requiring or implying any actual such relationship or order between such entities or actions.

Phrases such as an aspect, the aspect, another aspect, some aspects, one or more aspects, an implementation, the implementation, another implementation, some implementations, one or more implementations, an embodiment, the embodiment, another embodiment, some embodiments, one or more embodiments, a configuration, the configuration, another configuration, some configurations, one or more configurations, the subject technology, the disclosure, the present disclosure, other variations thereof and alike are for convenience and do not imply that a disclosure relating to such phrase(s) is essential to the subject technology or that such disclosure applies to all configurations of the subject technology. A disclosure relating to such phrase(s) may apply to all configurations, or one or more configurations. A disclosure relating to such phrase(s) may provide one or more examples. A phrase such as an aspect or some aspects may refer to one or more aspects and vice versa, and this applies similarly to other foregoing phrases.

A phrase "at least one of" preceding a series of items, with the terms "and" or "or" to separate any of the items, modifies the list as a whole, rather than each member of the list. The phrase "at least one of" does not require selection of at least one item; rather, the phrase allows a meaning that includes at least one of any one of the items, and/or at least one of any combination of the items, and/or at least one of each of the items. By way of example, each of the phrases "at least one of A, B, and C" or "at least one of A, B, or C" refers to only A, only B, or only C; any combination of A, B, and C; and/or at least one of each of A, B, and C.

It is understood that the specific order or hierarchy of steps, operations, or processes disclosed is an illustration of exemplary approaches. Unless explicitly stated otherwise, it is understood that the specific order or hierarchy of steps, operations, or processes may be performed in different order. Some of the steps, operations, or processes may be performed simultaneously. The accompanying method claims, if any, present elements of the various steps, operations or processes in a sample order, and are not meant to be limited to the specific order or hierarchy presented. These may be performed in serial, linearly, in parallel or in different order. It should be understood that the described instructions, operations, and systems can generally be integrated together in a single software/hardware product or packaged into multiple software/hardware products.

In one aspect, a term coupled or the like may refer to being directly coupled. In another aspect, a term coupled or the like may refer to being indirectly coupled.

Terms such as top, bottom, front, rear, side, horizontal, vertical, and the like refer to an arbitrary frame of reference, rather than to the ordinary gravitational frame of reference. Thus, such a term may extend upwardly, downwardly, diagonally, or horizontally in a gravitational frame of reference.

The disclosure is provided to enable any person skilled in the art to practice the various aspects described herein. In some instances, well-known structures and components are shown in block diagram form in order to avoid obscuring the concepts of the subject technology. The disclosure provides various examples of the subject technology, and the subject technology is not limited to these examples. Various modifications to these aspects will be readily apparent to those skilled in the art, and the principles described herein may be applied to other aspects.

All structural and functional equivalents to the elements of the various aspects described throughout the disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for".

The title, background, brief description of the drawings, abstract, and drawings are hereby incorporated into the disclosure and are provided as illustrative examples of the disclosure, not as restrictive descriptions. It is submitted with the understanding that they will not be used to limit the scope or meaning of the claims. In addition, in the detailed description, it can be seen that the description provides illustrative examples and the various features are grouped together in various implementations for the purpose of streamlining the disclosure. The method of disclosure is not to be interpreted as reflecting an intention that the claimed subject matter requires more features than are expressly recited in each claim. Rather, as the claims reflect, inventive subject matter lies in less than all features of a single disclosed configuration or operation. The claims are hereby incorporated into the detailed description, with each claim standing on its own as a separately claimed subject matter.

The claims are not intended to be limited to the aspects described herein, but are to be accorded the full scope consistent with the language of the claims and to encompass all legal equivalents. Notwithstanding, none of the claims are intended to embrace subject matter that fails to satisfy the requirements of the applicable patent law, nor should they be interpreted in such a way.

What is claimed is:

1. A stent system, the system comprising:
    a connector having a connector lumen;
    an elongated outer shaft fixedly coupled to an outer shaft hub, the outer shaft hub being fixedly coupled to the connector, the outer shaft having an outer shaft lumen;
    an elongated pusher shaft slidably disposed within the outer shaft lumen and the connector lumen and fixedly coupled to a pusher shaft hub, the pusher shaft having a first pusher shaft lumen and a second pusher shaft lumen, each of the first pusher shaft lumen and the second pusher shaft lumen extending from a proximalmost end of the pusher shaft to a distalmost end of the pusher shaft;
    an elongated inner shaft slidably disposed within the first pusher shaft lumen and having an inner lumen;
    a stabilizing wire slidably disposed within the second pusher shaft lumen; and
    a stent comprising barbs, wherein the stabilizing wire is fixedly coupled by a weld or a clamp to a proximal end of the stent such that the stabilizing wire and the stent are configured remain coupled together as the stabilizing wire slides with respect to the elongated outer shaft and the stent self-expands to a deployed state with the barbs extending radially outwardly to penetrate a portion of a body lumen for a temporary period upon delivery to a target location within a human patient, the elongated inner shaft extending through a lumen of the stent.

2. The system of claim 1, further comprising a balloon slidably disposed within the inner lumen.

3. The system of claim 1, wherein the pusher shaft hub further comprises a first mating feature and the stabilizing wire further comprises a second mating feature, the first mating feature sized and shaped to engage with the second mating feature.

4. The system of claim 1, wherein the inner lumen is partially sheathed by the inner shaft.

5. The system of claim 1, wherein the second pusher shaft lumen is partially sheathed by a portion of the pusher shaft.

6. The system of claim 1, wherein the stent comprises:
    a radially expandable cylindrical frame having struts; and
    the barbs carried by the struts.

7. A system for delivering, deploying, and recapturing a stent within a body lumen of a patient, the system comprising:
    the stent;
    an elongated outer shaft configured to sheath at least a zone of the stent;
    an outer shaft hub configured to proximally retract and/or distally advance the outer shaft;
    an elongated pusher shaft configured to distally advance the stent, the stent being fixedly coupled to the elongated pusher shaft, wherein the pusher shaft has a first pusher shaft lumen and a second pusher shaft lumen;
    a pusher shaft hub configured to proximally retract and/or distally advance the pusher shaft such that the pusher shaft and the stent are slidable together with respect to the elongated outer shaft;
    an elongated inner shaft slidably disposed within the first pusher shaft lumen and having an inner lumen, the elongated inner shaft extending through a lumen of the stent; and
    a stabilizing wire slidably disposed within the second pusher shaft lumen, wherein the stabilizing wire is fixedly coupled by a weld or a clamp to a proximal end of the stent such that the stabilizing wire and the stent are configured remain coupled together as the stabilizing wire slides with respect to the elongated outer shaft,
    wherein the stent is self-expanding to transform between a low-profile delivery state and an expanded deployed state for a temporary period, and
    wherein, in the deployed state, a plurality of barbs carried by one or more struts extend radially outwardly away from the struts and are configured to penetrate a first portion of the body lumen.

8. The system of claim 7, further comprising an elongated inner shaft configured to position a guidewire within the body lumen, the inner shaft having a partially enclosed inner shaft lumen partially configured to release the guidewire.

9. The system of claim 8, wherein the guidewire is configured to be released to remove a first catheter from the system and insert a second catheter into the system.

10. The system of claim 7, further comprising a balloon configured to expand when positioned within a lumen of the stent.

11. The system of claim 7, further comprising a strain relief element configured to prevent a first of the outer shaft from collapsing upon a second portion of the outer shaft.

12. The system of claim 7, wherein the pusher shaft is configured to prevent the stent from advancing proximally while the stent is transitioned from the delivery state to the deployed state.

13. The system of claim 7, wherein the stent is further configured to transform from the deployed state to a low-profile removal state, and in the removal state, the plurality of barbs retract inwardly toward the struts, and the outer shaft is configured to resheath the stent.

14. The system of claim 7, wherein
the stent comprises a radially self-expanding cylindrical frame, the plurality of barbs being circumferentially spaced apart from each other along a circumference formed by the one or more struts and extending radially in the expanded deployed state of the stent to penetrate the first portion of the body lumen, the plurality of barbs being distributed along a length of the frame between a proximal end and a distal end of the stent.

15. A delivery system for an expandable element, the delivery system comprising:
a connector having a connector lumen;
an outer shaft hub;
an elongated outer shaft fixedly coupled to the outer shaft hub, the outer shaft hub being fixedly coupled to the connector, wherein the elongated outer shaft includes an outer shaft lumen;
the expandable element carried within a distal portion of the elongated outer shaft and configured for delivery for a temporary period to a target location within a human patient, the expandable element comprising a radially self-expanding cylindrical frame having struts and barbs carried by the struts, the barbs being circumferentially spaced apart from each other along a circumference formed by the struts and extending radially in a deployed state of the expandable element to penetrate a portion of a body lumen, the barbs being distributed along a length of the frame between a proximal end and a distal end of the expandable element;
a stabilizing wire slidably disposed within the outer shaft lumen and extending through an opening in the connector, wherein a distal portion of the stabilizing wire is fixedly coupled by a weld or a clamp to the proximal end of the expandable element at which all of the struts of the frame are joined together such that all of the struts converge at the stabilizing wire; and
an elongated inner shaft slidably disposed within the outer shaft lumen and extending through the expandable element, wherein the stabilizing wire, the proximal end of the expandable element, and the distal end of the expandable element are slidable together with respect to the elongated outer shaft and the elongated inner shaft.

16. The delivery system of claim 15, wherein the expandable element, a portion of the expandable element, the barbs, a portion of the barbs, a portion of each of the barbs, or a combination thereof are biodegradable.

17. The delivery system of claim 15, wherein the stabilizing wire is configured to maintain a position of the expandable element at the target location within the patient during therapy.

18. The delivery system of claim 15, wherein the stabilizing wire is configured to maintain a position of the expandable element while the elongated outer shaft, the elongated inner shaft, a different shaft, or a combination thereof is intravascularly positioned within the human patient.

* * * * *